(12) United States Patent
Weaver

(10) Patent No.: US 9,067,894 B1
(45) Date of Patent: Jun. 30, 2015

(54) COMPOUND, COMPOSITION, AND METHOD OF ACTIVATING GIRK POTASSIUM CHANNEL AND USE OF SAME FOR TREATING CONDITIONS OF INTEREST

(71) Applicant: Vanderbilt University, Nashville, TN (US)

(72) Inventor: C. David Weaver, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/201,331

(22) Filed: Mar. 7, 2014

Related U.S. Application Data

(60) Provisional application No. 61/774,142, filed on Mar. 7, 2013.

(51) Int. Cl.
| | | |
|---|---|---|
| *C07D 231/40* | (2006.01) | |
| *A61K 31/18* | (2006.01) | |
| *A61K 31/415* | (2006.01) | |
| *A61K 45/06* | (2006.01) | |
| *C07C 311/16* | (2006.01) | |

(52) U.S. Cl.
CPC .............. *C07D 231/40* (2013.01); *A61K 31/18* (2013.01); *A61K 31/415* (2013.01); *A61K 45/06* (2013.01); *C07C 311/16* (2013.01)

(58) Field of Classification Search
None
See application file for complete search history.

(56) References Cited

U.S. PATENT DOCUMENTS 6,228,881 B1 * 5/2001 Regan et al. .................. 514/432

OTHER PUBLICATIONS

Logothetis, D. E., Kurachi, Y., Galper, J., Neer, E. J. & Clapham, D. E. The βγ subunits of GTP-binding proteins activate the muscarinic K+ channel in heart. Nature325, 321-326 (1987).
Kubo Y, Reuveny E, Slesinger PA, Jan YN, Jan LY. (1993) Primary structure and functional expression of a rat G-protein-coupled muscarinic potassium channel. Nature. 364(6440):802-6.
Wickman, K. D. et al. Recombinant G-protein βγ-subunits activate the muscarinic-gated atrial potassium channel. Nature 368, 255-257 (1994).
Reuveny E. et al. Activation of the cloned muscarinic potassium channel by G protein βγ subunits. Nature370, 143-146 (1994).
Lesage F et al. (1994) Cloning provides evidence for a family of inward rectifier and G-protein coupled K+ channels in the brain. FEBS Lett. 353(1):37-42.
Krapivinsky G et al. (1995) the G-protein-gated atrial K+ channel IKACh is a heteromultimer of two inwardly rectifying K(+)-channel proteins. Nature. 374(6518):135-41.
Luscher C & Slesinger P (2010) Emerging roles for G protein-gated inwardly rectifying potassium (GIRK) channels in health and disease. Nat Rev Neurosci. 11:301-315.
Kloukina V, Herzer S, Karlsson N, Perez M, Daraio T, Meister B. (2012) G-protein-gated inwardly rectifying K+ channel 4 (GIRK4) immunoreactivity in chemically defined neurons of the hypothalamic arcuate nucleus that control body weight. J Chem Neuroanat. 44(1):14-23.
Hedin KE, Lim NF & Clapham DE. (1996) Cloning of a *Xenopus laevis* inwardly rectifying K+ channel subunit that permits GIRK1 expression of IKACh currents in oocytes. Neuron 16(2):423-9.
Inanobe, A. et al. (1999) Characterization of G-protein-gated K+ channels composed of Kir3.2 subunits in dopaminergic neurons of the substantia nigra. J. Neurosci. 19, 1006-1017.
Cruz, H. G. et al. Bi-directional effects of GABAB receptor agonists on the mesolimbic dopamine system. Nature Neurosci. 7, 153-159 (2004).
Fernández-Alacid L, et al. (2009) Subcellular compartment-specific molecular diversity of pre- and post-synaptic GABA-activated GIRK channels in Purkinje cells. J Neurochem. 110(4):1363-76.
Lujan R, Maylie J & Adelman J. (2009) New sites of action for GIRK and SK channels. Nat Rev Neurosci. 10:475-480.
Yamada K et al. (2012) Association study of the KCNJ3 gene as a susceptibility candidate for schizophrenia in the Chinese population. Hum Genet. 131(3):443-51.
Nishizawa D et al. (2009) Association between KCNJ6 (GIRK2) gene polymorphisms and postoperative analgesic requirements after major abdominal surgery. PLoS One. 4(9):e7060.
Smith SB et al. (2008) Quantitative trait locus and computational mapping identifies Kcnj9 (GIRK3) as a candidate gene affecting analgesia from multiple drug classes. Pharmacogenet Genomics. 18(3):231-41.
Kang SJ, et al. (2012) Family-based genome-wide association study of frontal theta oscillations identifies potassium channel gene KCNJ6. Genes Brain Behav. 712-9.
Jabbari J, Olesen MS, Holst AG, Nielsen JB, Haunso S & Svendsen JH. (2011) Common polymorphisms in KCNJ5 are associated with early-onset lone atrial fibrillation in Caucasians. Cardiology. 118(2):116-20.
Zennaro MC & Jeunemaitre X. (2011) Mutations in KCNJ5 gene cause hyperaldosteronism. Circ Res. 108(12):1417-8.
Bhave G, Lonergan D, Chauder BA & Denton JS. (2010) Small-molecule modulators of inward rectifier K+ channels: recent advances and future possibilities. Future Med Chem. 2(5):757-74.
Machida T et al. (2011) Effects of a highly selective acetylcholine-activated K+ channel blocker on experimental atrial fibrillation. Circ Arrhythm Electrophysiol. 4(1):94-102.
Kobayashi T et al. (1999) Ethanol opens G-protein-activated inwardly rectifying K+ channels. Nat Neurosci. 2 (12):1091-7.
Aryal P, Dvir H, Choe S & Slesinger PA. (2009) A discrete alcohol pocket involved in GIRK channel activation. Nat Neurosci. 12(8):988-95.
Yow TT et al. (2011) Naringin directly activates inwardly rectifying potassium channels at an overlapping binding site to tertiapin-Q. Br J Pharmacol.163(5):1017-33.
Nishizawa D, Gajya N & Ikeda K. (2011) Identification of selective agonists and antagonists to g protein-activated inwardly rectifying potassium channels: candidate medicines for drug dependence and pain. Curr Neuropharmacol. 9 (1):113-7.
Niswender CM et al. (2008) A novel assay of Gi/o-linked G protein-coupled receptor coupling to potassium channels provides new insights into the pharmacology of the group III metabotropic glutamate receptors. Mol Pharmacol. 73 (4):1213-24.

(Continued)

*Primary Examiner* — Kamal Saeed
(74) *Attorney, Agent, or Firm* — Stites & Harbison PLLC; Mandy Wilson Decker

(57) ABSTRACT

The present invention provides small molecule activators of GIRK potassium channels and methods for use thereof.

18 Claims, 15 Drawing Sheets

(56) References Cited

OTHER PUBLICATIONS

Kennedy, JP et al. Application of combinatorial chemistry science on modern drug discovery. J. Comb. Chem. 2008, 10, 345-354.

Rubinstein M et al. (2009) Divergent regulation of GIRK1 and GIRK2 subunits of the neuronal G protein gated K+ channel by Gαi GDP and Gβγ. J Physiol 587(14): 3473-3491.

Signorini, S., Liao, Y. J., Duncan, S. A., Jan, L. Y. & Stoffel, M. (1997) Normal cerebellar development but susceptibility to seizures in mice lacking G protein-coupled, inwardly rectifying K+ channel GIRK2. Proc. Natl Acad. Sci. USA 94, 923-927.

Khroyan TV et al. Rodent Motor and Neuropsychological Behavior Measured in Home Cages Using the Integrated Modular Platform—SmartCageTM. Clinical and Experimental Pharmacology and Physiology, 2012, 39, 614-622.

Kobayashi, T.; Ikeda, K.; Ichikawa, T.; Abe, S.; Togashi, S.; Kumanishi, T. Biochem. Biophys. Res. Commun. 1995, 208, 1166.

Karschin, C.; Dissmann, E.; Stuhmer, W.; Karschin, A. J. Neurosci. 1996, 16, 3559.

Kaufmann, K., et al., (2013) ML297 (VU0456810), the First Potent and Selective Activator of the GIRK Potassium Channel, Displays Antiepileptic Properties in Mice. ACS Chemical Neuroscience. 4, 1278-1286.

Lindsley, C. W.; Wisnoski, D. D.; Leister, W. H.; O'Brien, J. A.; Lemiare, W.; Williams, D. L., Jr.; Burno, M.; Sur, C.; Kinney, G. G.; Pettibone, D. J.; Tiller, P. R.; Smith, S.; Duggan, M. E.; Hartman, G. D.; Conn, P. J.; Huff, J. R. J. Med. Chem. 2004, 47, 5825.

Sharma, S.; Rodriguez, A.; Conn, P. J.; Lindsley, C. W. Bioorg. Med. Chem. Lett. 2008, 18, 4098.

Wood, M. R.; Hopkins, C. R.; Brogan, J. T.; Conn, P. J.; Lindsley, C. W. Biochemistry 2011, 50, 2403.

Cheung, Y.-Y.; Yu, H.; Xu, K.; Zou, B.; Wu, M.; McManus, O. B.; Li, M.; Lindsley, C. W.; Hopkins, C. R. J. Med. Chem. 2012, 55, 6975.

Terry, P.; Katz, J. L. Psychopharmacology 1994, 113, 328.

O'Neil, S. K.; Bolger, G. T. Brain Res. Bull. 1988, 21, 865.

\* cited by examiner

COMPOUND, COMPOSITION, AND METHOD OF ACTIVATING GIRK POTASSIUM CHANNEL AND USE OF SAME FOR TREATING CONDITIONS OF INTEREST

RELATED APPLICATIONS

This application claims priority from U.S. Provisional Application Ser. No. 61/774,142 filed Mar. 7, 2013, the entire disclosure of which is incorporated herein by this reference.

GOVERNMENT INTEREST

This invention was made with government support under MH074427, MH084659, and MH076398, each awarded by the National Institutes of Health (NIH). The government has certain rights in the invention.

TECHNICAL FIELD

The presently-disclosed subject matter relates to compounds, compositions, and methods for activating a GIRK potassium channel. In particular, the presently-disclosed subject matter relates to activating a GIRK potassium channel including a GIRK1 subunit.

INTRODUCTION

The G-protein activated inward rectifying potassium ($K^+$) channels, GIRKs, are members of a larger family of inward-rectifying potassium channels, $K_{ir}$s. As the name suggests, GIRK channels can be activated by pertussis toxin-sensitive G-protein-coupled receptors of the $G_i$ subtype through interactions with the G-protein's β/γ subunits[1-3]. However, GIRK regulation is complex and both positive and negative modulation has been observed through $G_s$ and $G_q$ GPCRs as well as via other indirect mechanisms. GIRK regulation by GPCRs is believed to be linked to biological effects of a variety of GPCR agonists including opioids, acetylcholine, and the $GABA_B$ receptor agonist, baclofen.

The GIRK channels are comprised of four subunits, GIRK1-4 (aka $K_{ir}$3.1-3.4)[4-5], encoded by the genes KCNJ3, KCNJ6, KCNJ9, and KCNJ5, respectively. These four subunits can form homo and heterotetramers with unique biophysical properties, regulation, and distribution (reviewed in[6]). GIRKs are found widely expressed in the brain with the GIRK1/2 subunit combination being the most common and widespread within the cortex, hippocampus, cerebellum, and various other brain regions, while other subunit combinations, such as GIRK1/4, show very limited expression in the brain with concentrations in discrete mid-brain nuclei such as the hypothalmus[7]. Although GIRK1 is widely expressed in the brain, it is not believed to form functional channels on its own[8]. However, there are GIRKs that have been reported that do not express GIRK1. These GIRKs, including homomeric GIRK2 and GIRK2/3, show restricted expression patterns in mid-brain regions such as ventral tegmental area (VTA) and substantia nigra[9,10]. Different GIRK subunit combinations also display distinct subcellular localization patterns, including pre, post, and extra-synaptic localization[11-12], perhaps underlying a diversity of physiological roles for GIRK and GIRK regulation. GIRK expression is not limited to the brain, however. Notably, the GIRK1/4 subunit combination is highly localized in cardiac atrial myocytes where it is responsible for the muscarinic acetylcholine activated current, IK Ach, involved in regulating heart rate. Because of GIRK1/4's restricted expression in atrial myocytes, it has long been thought to serve as a potential target for the treatment of atrial fibrillation.

A number of studies using subunit-specific GIRK knock-out mice have produced a wide variety of interesting phenotypes that suggest roles for GIRKs in a variety of important physiological processes as well as pointing to GIRK as a target for therapeutic intervention6. Among these are effects on addiction and withdrawal behaviors, pain perception, anxiety, spatial learning/memory, and predisposition toward seizure activity. In addition to these GIRK knockout phenotypes, emerging human genetic evidence is accumulating that may further implicate GIRK in human disease. Recent studies link GIRK1 to schizophrenia susceptibility in a Chinese population[13]; in this study, lower GIRK1 expression levels in postmortem brains from schizophrenic and bipolar individuals were observed. Other studies have suggested GIRK2 and GIRK3's involvement in responsiveness to analgesics[14-15], GIRK2's potential link to alcoholism[16], as well as links between GIRK4 and early-onset atrial fibrillation[17] and hypoaldosteronism[8].

Although GIRKs have long been the focus of basic research efforts providing mounting evidence to linkages to human disease, there are very few pharmacological tools that have been reported[19] that might allow a better understanding of the roles of GIRKs in normal and pathophysiological conditions. This lack of tools has also limited understanding of GIRKs' potential as targets for therapeutic intervention. In the GIRK inhibitor class, the compound NTC-801 stands as the sole example of a highly potent and selective GIRK compound[20]. This compound, with a slight preference for the predominant cardiac form of GIRK, GIRK1/4, is presently in clinical trials for the treatment of atrial fibrillation. In addition to GPCR-mediated activation, GIRKs are also known to be activated by alcohols, including ethanol[21-22], which may exert some of its behavioral effects through its action on GIRK. Ethanol exerts effects on many channels, including NMDA and GABAA receptors; therefore, ethanol is not a specific GIRK activator. Two recent reports have disclosed additional compounds that activate GIRK[23-24]. In the case of the natural product, naringin, a potency of ~100 µM limits the utility of the compound to in vitro assays. Both GIRK inhibitors and activators have been identified by screening a library of compounds that are structurally related to fluoxetine[23]. In the case of these compounds, the lack of structural information and other details regarding their activity and specificity preclude any substantive conclusions regarding the use of these compounds as tools to study GIRKs in vivo or in vitro.

An HTS-compatible thallium flux assay has been developed for Gi/o-coupled GPCRs using GIRK as a readout[24]. This assay technology was used to conduct a high-throughput screen in cells co-expressing metabotropic glutamate receptor 8 (mGlu8) and GIRK1/2 channels with the molecular libraries small molecule repository (MLSMR) compound collection as part of the Molecular Libraries Screening Center Network (MLSCN). In an effort to identify novel GIRK modulators, the hits from the primary screening set were evaluated for their ability to activate GIRK irrespective of modulation by a GPCR. This exercise led to the identification of a GIRK activator with micromolar potency. This compound, CID736191, was refined using medicinal chemistry to arrive at a GIRK-selective probe with sub-micromolar potency, the ability to activate GIRK in the presence of *bordetella pertussis* toxin, and pharmacokinetic properties suitable for testing in vivo.

Together, the body of GIRK research implicates GIRK in processes as diverse as controlling heart rhythm, to effects on reward/addiction, to modulation of response to analgesics. Despite years of GIRK-focused research, very few tools exist with which to selectively modulate GIRK channels' activity and until now no tools existed that potently and selectively activated GIRKs. There remains a need in the art for a GIRK activators, including GIRK activators having specificity for particular GIRK subunit(s).

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compounds, compositions, methods, and kits having for activating GIRK potassium channels, particularly GIRK potassium channels including a GIRK1 subunit, and for treating certain conditions of interest, for example, epilepsy.

The presently-disclosed subject matter includes a compound having a structure represented by the formula

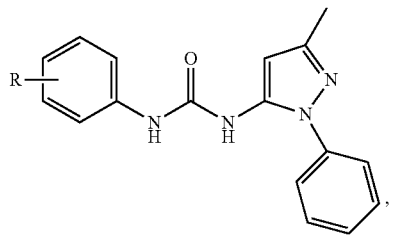

or a pharmaceutically-acceptable salt thereof, wherein R is selected from H, 2-Cl, 3-Cl, 4-Cl, 2-Br, 3-Br, 4-Br, 3-F, 4-F, 2-CF$_3$, 3-CF$_3$, 4-CF$_3$, 3-CH$_3$, 2-SCH$_3$, 3-SO$_2$NH$_2$, 4-SO$_2$NH$_2$, 3-SCH$_3$, 4-SCH$_3$, 2-OCH$_3$, 3-OCH$_3$, 4-OCH$_3$, 3,4-diCl, 3,5-diCl, 2-Cl/6-OCH$_3$, and 3,4-diF. In some embodiments, the compound is

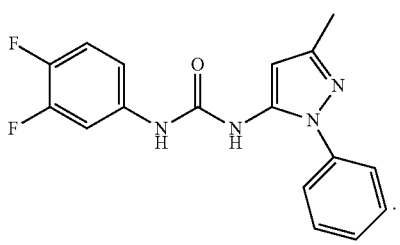 [SMILES: Cc1cc(NC(=O)Nc2ccc(F)c(F)c2)n(-c2ccccc2)n1]

The presently-disclosed subject matter includes a compound having a structure represented by the formula

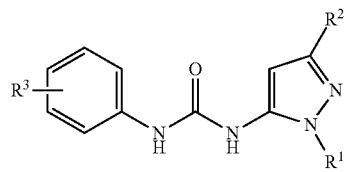

wherein R1 is selected from

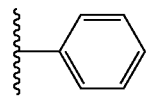

and

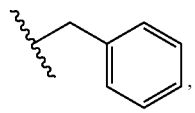

R2 is selected from

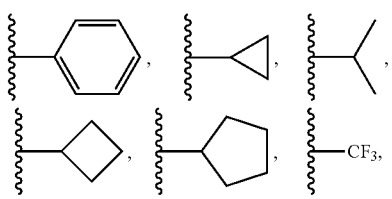

and

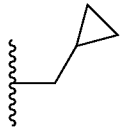

and R3 is selected from 3-Cl, 3-Br, 3-CH$_3$, 4-CH$_3$, 3-F, 4-F, 3, 4-diF, 3-SCH$_3$, 3-CF$_3$, and 3-Cl/4-F. In some embodiments, the compound is

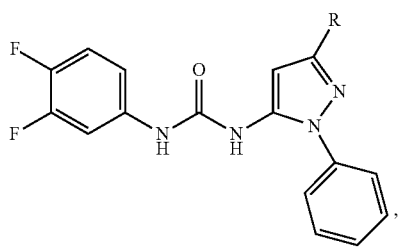

wherein R is selected from

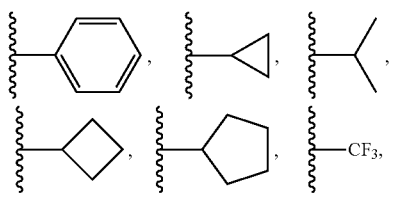

and

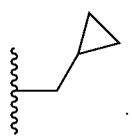

The presently-disclosed subject matter includes a compound having a structure represented by the formula

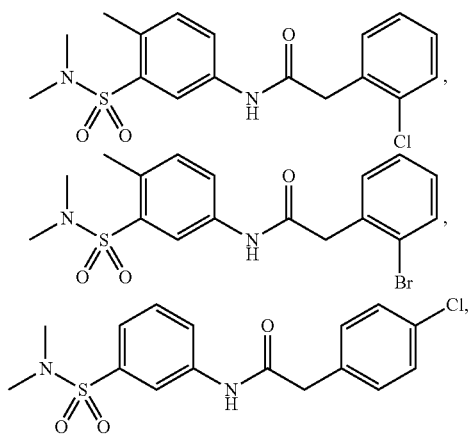

or

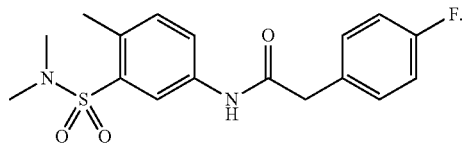 [SMILES: Cc1ccc(NC(=O)Cc2ccc(F)cc2)cc1S(=O)(=O)N(C)C]

The presently-disclosed subject matter includes a compound having a structure represented by the formula

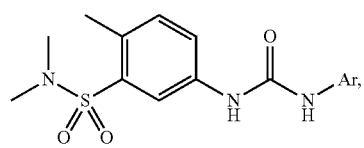

wherein AR is selected from Ph, 4-CLPh, 3-CL/4-MePH, 4-OMePh, 2-FPh, 3-FPh, 2-ClPh, 4-CF$_3$Ph, 2,5-DiOMePh, and 3-CNPH.

The presently-disclosed subject matter includes a compound having a structure represented by the formula

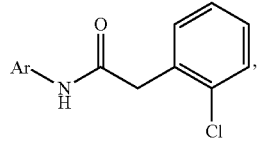

wherein Ar is selected from 4-F/3-SO$_2$MePh, 3-t-BuPh, 3-OCHF$_2$Ph, 3-Cl/5-CF$_3$Ph, 4-Cl/5-CF$_3$Ph, 3-ClPh, 4-ClPh, 4-CF$_3$Ph, and 3-MePh.

The presently-disclosed subject matter further includes pharmaceutical compositions of each of the compounds disclosed herein. Such pharmaceutical compositions can include the compound and a pharmaceutically-acceptable carrier. In some embodiments, the pharmaceutical composition can also include a second compound or composition having GIRK activation activity, or wherein the second compound or composition is useful for treating a condition of interest, selected from addiction and withdrawal behaviors, pain perception, anxiety, spatial learning/memory, and predisposition toward seizure activity.

Compounds and pharmaceutical compositions disclosed herein can be GIRK activators, and in this regard, can activate GIRK channels. In some embodiments the compound of composition activates GIRK channels including a GIRK1 subunit. In some embodiments the compound or composition does not activate GIRK channels that do not include a GIRK1 subunit. In some embodiments, the compound or composition activates GIRK channels selected from GIRK1/2, GIRK1/3, and GIRK1/4. In some embodiments, the compound or composition activates GIRK 2, but not GIRK 4. In some embodiments, the compound or composition activates GIRK 4, but not GIRK 2. In some embodiments, the compound or composition activates GIRK 2, but not GIRK 3. In some embodiments, the compound or composition activates GIRK 3, but not GIRK 2. In some embodiments, the compound or composition activates GIRK 3, but not GIRK 4. In some embodiments, the compound or composition activates GIRK 3, but not GIRK 3.

The presently-disclosed subject matter further includes methods employing the compounds and compositions as disclosed herein. The presently-disclosed subject matter includes a method of activating a GIRK potassium channel, which involves contacting a cell with an effective amount of a compound or pharmaceutical composition disclosed herein. In some embodiments, contacting the cell with the compound or composition comprises administering the compound or composition to a subject. In some embodiments, the administration is to a subject in need of treatment for a condition of interest. In some embodiments, the condition of interest is selected from addiction and withdrawal behaviors, pain perception, anxiety, spatial learning/memory, predisposition toward seizure activity, e.g., epilepsy, and other conditions disclosed herein below.

In some embodiments, the presently-disclosed subject matter includes a method of activating a GIRK potassium channel, which involves contacting a cell with an effective amount of a compound or composition disclosed herein. In some embodiments, contacting the cell with the compound or composition activates GIRK channels selected from GIRK1/2, GIRK1/3, and GIRK1/4. In some embodiments, the compound or composition activates GIRK 2, but not GIRK 4. In some embodiments, the compound or composition activates GIRK 4, but not GIRK 2. In some embodiments, the compound or composition activates GIRK 2, but not GIRK 3. In some embodiments, the compound or composition activates GIRK 3, but not GIRK 2. In some embodiments, the compound or composition activates GIRK 3, but not GIRK 4. In some embodiments, the compound or composition activates GIRK 3, but not GIRK 3.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 9. GIRK activator concentration response curves (CRC) measuring thallium flux. (A) GIRK1/2 (EC50=1.1 LM, 110%) and GIRK1/4 (EC50=1.1 LM, 104%) CRCs for the HTS hit 3; (B) GIRK1/2 (EC50=1.4 LM, 108%) and GIRK1/4 (EC50=1.6 LM, 114%) CRC for related analog 3a.

DESCRIPTION OF EXEMPLARY EMBODIMENTS

Figure 1:
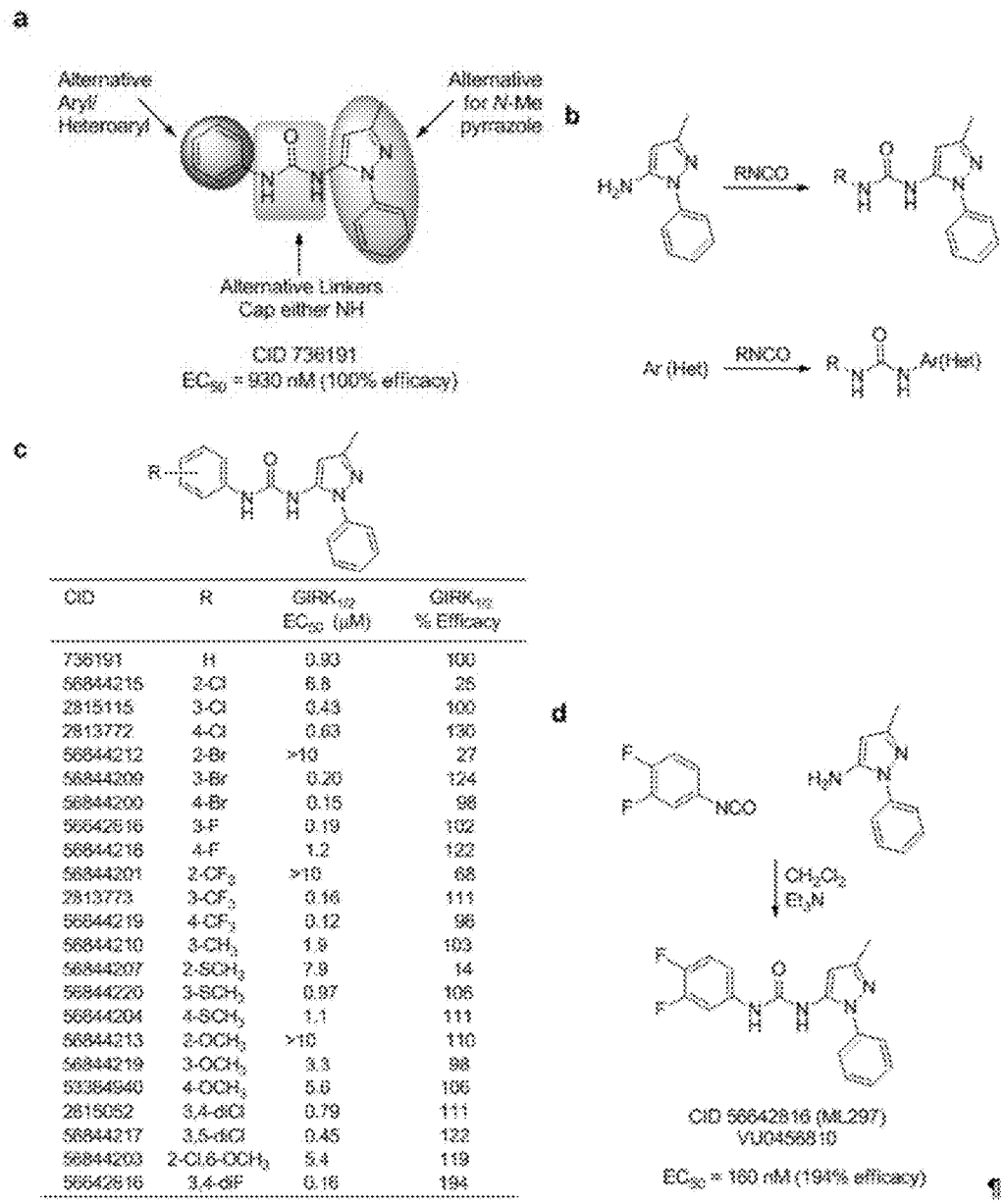
FIG. 1. Design, synthetic strategy and SAR leading to the discovery of the GIRK activator VU0456810. (a) Diversity-oriented modular design strategy to survey three regions of HTS hit CID 736191. (b) General synthetic approach for library synthesis. (c) SAR table of analogs of CID 736191. (d) Synthesis and structure of VU0456810 (CID 56642816, ML297). Potency values were obtained from triplicate determinations and the efficacy values shown are standardized to the efficacy of the parent compound in the series, CID736191, arbitrarily designated as 100%.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compounds, compositions, methods, and kits having for activating GIRK potassium channels, particularly GIRK potassium channels including a GIRK1 subunit, and for treating certain conditions of interest, for example, epilepsy.

The presently-disclosed subject matter includes a compound having a structure represented by the formula:

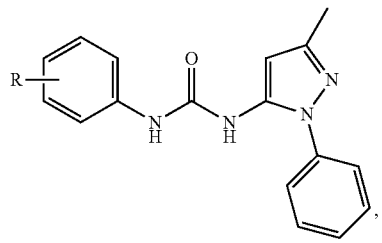

or a pharmaceutically-acceptable salt thereof, wherein R is selected from H, 2-Cl, 3-Cl, 4-Cl, 2-Br, 3-Br, 4-Br, 3-F, 4-F, 2-CF$_3$, 3-CF$_3$, 4-CF$_3$, 3-CH$_3$, 2-SCH$_3$, 3-SO$_2$NH$_2$, 4-SO$_2$NH$_2$, 3-SCH$_3$, 4-SCH$_3$, 2-OCH$_3$, 3-OCH$_3$, 4-OCH$_3$, 3,4-diCl, 3,5-diCl, 2-Cl/6-OCH$_3$, and 3,4-diF. In some embodiments, the compound has a structure represented by the formula:

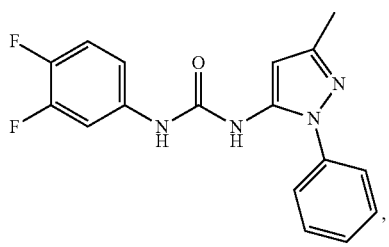 [SMILES: Cc1cc(NC(=O)Nc2ccc(F)c(F)c2)n(-c2ccccc2)n1]

or a pharmaceutically-acceptable salt thereof.

The presently-disclosed subject matter further includes a compound having a structure represented by the formula:

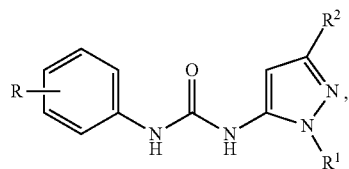

or a pharmaceutically-acceptable salt thereof, wherein R1 is selected from

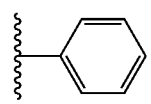

and

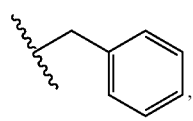 [SMILES: *Cc1ccccc1]

R2 is selected from

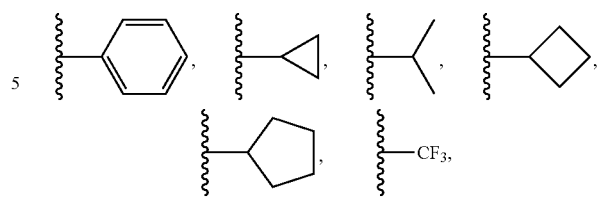

and

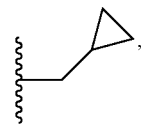

and R3 is selected from 3-Cl, 3-Br, 3-CH$_3$, 4-CH$_3$, 3-F, 4-F, 3,4-diF, 3-SCH$_3$, 3-CF$_3$, and 3-Cl/4-F. In some embodiments, the compound has a structure represented by the formula:

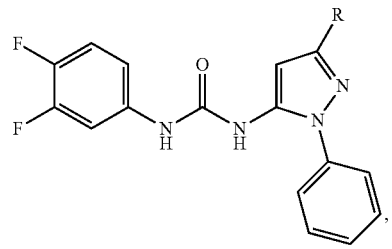

or a pharmaceutically-acceptable salt thereof, wherein R is selected from

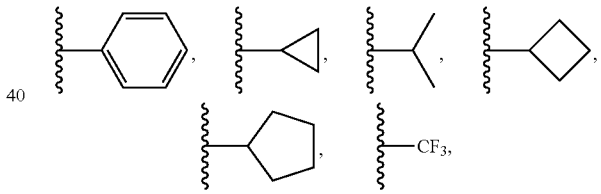

and

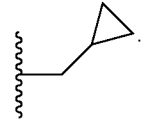 [SMILES: *CC1CC1]

The presently-disclosed subject matter further includes a compound having a structure represented by the formula:

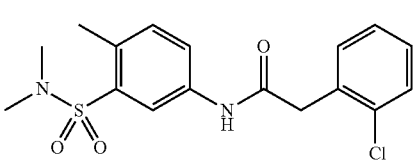 [SMILES: Cc1ccc(NC(=O)Cc2ccccc2Cl)cc1S(=O)(=O)N(C)C]

or a pharmaceutically-acceptable salt thereof. The presently-disclosed subject matter further includes a compound having a structure represented by the formula:

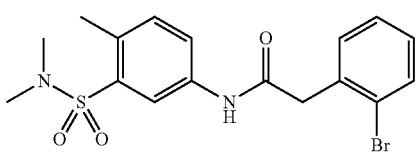 [SMILES: Cc1ccc(NC(=O)Cc2ccccc2Br)cc1S(=O)(=O)N(C)C]

or a pharmaceutically-acceptable salt thereof. The presently-disclosed subject matter further includes a compound having a structure represented by the formula:

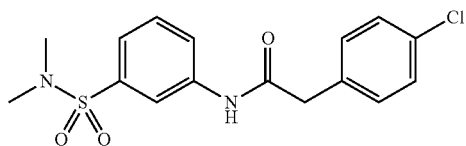 [SMILES: CN(C)S(=O)(=O)c1cccc(NC(=O)Cc2ccc(Cl)cc2)c1]

or a pharmaceutically-acceptable salt thereof. The presently-disclosed subject matter further includes a compound having a structure represented by the formula:

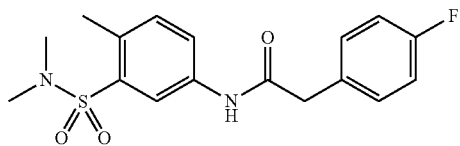 [SMILES: Cc1ccc(NC(=O)Cc2ccc(F)cc2)cc1S(=O)(=O)N(C)C]

or a pharmaceutically-acceptable salt thereof. The presently-disclosed subject matter further includes a compound having a structure represented by the formula:

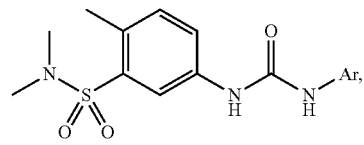

or a pharmaceutically-acceptable salt thereof, wherein AR is selected from Ph, 4-CLPh, 3-CL/4-MePH, 4-OMePh, 2-FPh, 3-FPh, 2-ClPh, 4-CF$_3$Ph, 2,5-DiOMePh, and 3-CNPH.

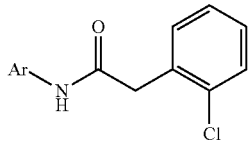

or a pharmaceutically-acceptable salt thereof, wherein Ar is selected from 4-F/3-SO$_2$MePh, 3-t-BuPh, 3-OCHF$_2$Ph, 3-Cl/5-CF$_3$Ph, 4-Cl/5-CF$_3$Ph, 3-ClPh, 4-ClPh, 4-CF$_3$Ph, and 3-MePh.

The presently-disclosed subject matter further includes pharmaceutical compositions of the compounds as disclosed herein, and further includes a pharmaceutically-acceptable carrier. In this regard, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

In some embodiments, the pharmaceutical composition includes a compound as disclosed herein, and a pharmaceutically-acceptable carrier.

As disclosed herein, compounds and compositions of the presently-disclosed subject matter are GIRK potassium channel activators. Such activators have further utilities as described herein, which include, but are not limited to, addiction and withdrawal behaviors, pain perception, anxiety, spatial learning/memory, sleep, and predisposition toward seizure activity. As such, in some embodiments, the pharmaceutical composition can further include a second compound or composition having GIRK activation activity, or wherein the second compound or composition is useful for treating a condition of interest, selected from addiction and withdrawal behaviors, pain perception, anxiety, spatial learning/memory, sleep, and predisposition toward seizure activity (e.g., epilepsy). In some embodiments, the pharmaceutical composition is useful for treating epilepsy.

As noted herein, the compound and pharmaceutical composition of the presently-disclosed subject matter have potency and selectivity that provide particular utility. In this regard, the compound can activate GIRK channels including a GIRK1 subunit. The compound has substantially no activation activity for GIRK channels that do not include a GIRK1 subunit. In some embodiments, the compound or pharmaceutical composition can be used to activate GIRK channels selected GIRK1/2, GIRK1/3, and GIRK1/4.

The presently-disclosed subject matter further includes kits, including a compound or pharmaceutical composition, as disclosed herein. In some embodiments, the kit can include a compound or pharmaceutical composition, as described herein, packaged together with a second compound or composition, a treatment device, and/or an administration device.

In some embodiments, the kit includes a compound or pharmaceutical composition, as disclosed herein, and further includes a second compound or composition having GIRK activation activity, or wherein the second compound or composition is useful for treating a condition of interest, selected from addiction and withdrawal behaviors, pain perception, anxiety, spatial learning/memory, and predisposition toward seizure activity (e.g., epilepsy).

The presently-disclosed subject matter further includes kits comprising a reagent to carry out a method as described herein.

The presently-disclosed subject matter further includes methods. A method of activating a GIRK potassium channel is provided. In some embodiments, the method includes contacting a cell with an effective amount of a compound or pharmaceutical composition as described herein. In some embodiments of the method, contacting the cell with the compound or composition involves administering the compound or composition to a subject. In some embodiments, the administration is to a subject in need of treatment for a condition of interest. In some embodiments, the condition of interest is selected from addiction and withdrawal behaviors, pain perception, anxiety, spatial learning/memory, and predisposition toward seizure activity (e.g., epilepsy). In some embodiments, the condition of interest is epilepsy.

Also provided is a method of treating epilepsy in a subject in need thereof, including administering to the subject an effective amount of a compound or pharmaceutical composition as described herein. In some embodiments, the compound activates GIRK channels selected from GIRK1/2, GIRK1/3, and GIRK1/4. In some embodiments, the compound activates GIRK channels selectively, e.g., GIRK 2 but not GIRK 4.

The presently-disclosed subject matter further includes a method for identifying potent and selective activators of a GIRK potassium channel including a GIRK1 subunit, and/or compounds useful for treating epilepsy, which involves contacting a test compound with a cell including GIRK potassium channel including a GIRK1 subunit, determining the GIRK1 activation activity of the compound, and comparing the activation activity of the test compound to the activation activity of a GIRK activator compound as identified herein.

As will be recognized by one of ordinary skill in the art, the term "activating" or "activation" does not refer to the ability to completely activate all target biological activity in all cases. Rather, the skilled artisan will understand that the term "activating" refers to increasing biological activity of a target, such as a GIRK potassium channel. Such increase in biological activity can be determined relative to a control, wherein an activator is not administered and/or placed in contact with the target. For example, in some embodiments, an increase in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or greater than 100% increase. The term "activator" refers to a compound of composition that activates or increases the biological activity of a target, such as a GIRK potassium channel. Without wishing to be bound by theory, the compounds could be activating the channels by affecting the probability that a channel will be open or not open at a given time point or time span. As such, as will be recognized by one of ordinary skill in the art, such activation could result in an increase in activity of greater than 100%, relative to a control.

The terms "treatment" or "treating" refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or other rodent (e.g., pigs, hamsters, gerbils, rats, mice, etc). The term does not denote a particular age or sex. Thus, adult and newborn subjects, as well as fetuses, whether male or female, are intended to be covered.

The term "administering" refers to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

Disclosed herein is a truly potent, effective, and selective GIRK activator, VU0456810 (ML297). VU0456810 displays little or no activity when tested against a variety of other ion channels and unexpectedly shows selectivity for GIRK channels containing the GIRK1 subunit. This surprising finding opens a door to better understanding differences in GIRK structure, function and regulation. VU0456810 is active in two in vivo models of epilepsy, a disease where up to 40% of patients remain with symptoms refractory to present treatments. The development of VU0456810 represents a truly significant advancement in the ability to selectively probe GIRK's role in physiology as wells as providing a tool for beginning to understand GIRK's potential as a target for a diversity of therapeutic indications, including epilepsy. Other indications of interest in this context include, but are not limited to, anxiety, pain, feeding, and addiction/withdrawal.

Results

Figure 2:
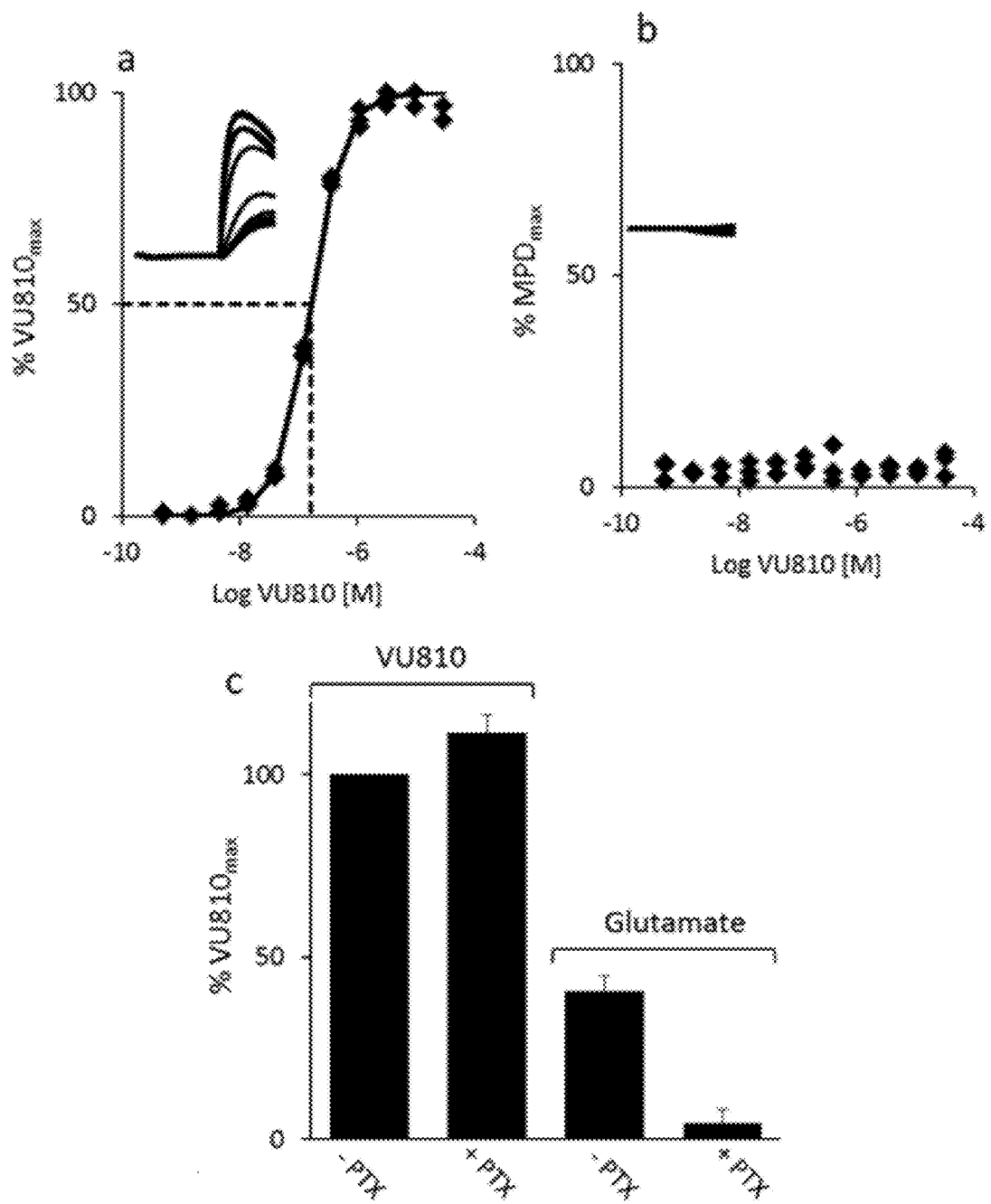
FIG. 2. VU0456810 (VU810) selectively activates GIRK1-containing GIRKs independent of active $G_i$ G-proteins. Shown in (a) are thallium flux data resulting from treating GIRK1+GIRK2 expressing cells with a VU0456810 concentration series. The fit shown is to triplicate data points from a representative experiment. The inset shows the raw traces from which fits were derived. Data are normalized to a maximally effective concentration of VU0456810. Shown in (b) are data obtained and plotted as in (a) for cells expressing GIRK2 alone. Data are normalized to a 78 mM concentration of the non-selective GIRK activator, methyl pentandiol. Shown in (c) are thallium flux traces obtained from pertussis toxin-treated GIRK1+GIRK2+mGlu$_8$-expressing cells in the presence of a maximally effective concentration of VU0456810 (10 μM) or a maximally effective concentration of glutamate (100 μM). All data shown are representative of at least three independent experiments.

The thallium flux-based HTS of mGlu8 using GIRK1/2 as a readout yielded ~2000 hits. These hits were tested at single concentrations in HEK-293 cells expressing either mGlu8 and GIRK1/2 or mGlu8 without GIRK in thallium flux assays. The hits were also tested in HEK-293 cells co-expressing mGlu8 and Gqi9 in a calcium flux assay (AIDs 623869, 623952). Compounds that were only active when tested on the cells co-expressing mGlu8 and GIRK1/2 were selected for further testing. From this effort (FIG. 1a), CID736191 (1) was identified, an asymmetrical urea, as a confirmed GIRK activator of GIRK1/2 with an EC50 of ~1 µM. The low-micromolar potency, combined with the modular nature of the chemotype, represented an attractive starting point for chemical optimization via iterative parallel synthesis25. Several libraries were prepared surveying alternative substituents on the aryl ring, alternative heterocycles to replace the N-phenyl pyrrazole, as well as alternative linkers for the urea moiety (FIG. 1b). Testing of these compounds using the thallium flux assay in cell lines expressing GIRK1/2, GIRK1/4 and GIRK2/3 (AIDS 623952, 602144, 602151, 602149, 602150) resulted in clear structure-activity-relationships (SAR). Some of the more active compounds include the N-phenyl pyrazole and both NH moieties of the urea linker. Productive SAR was discovered by appending substituents to the western aryl ring. Here, 2-substituents generally lead to inactive compounds, whereas 3-substituted and 3,4-disubstituted analogs proved to be optimal (FIG. 1c). Thus, chemical optimization afforded VU0456810 (aka VU0456810, CID 56642816, ML297), as the first highly potent GIRK-activator (FIG. 1d). As shown in FIG. 2a, in thallium flux assays VU0456810 showed concentration-dependent efficacy when tested on cells expressing GIRK1/2 with a measured potency of ~160 nM. VU0456810 was also able to activate GIRK channels comprised of GIRK1/3 and GIRK1/4 subunit combinations (Table 1a). However, VU0456810 showed a complete inability to modulate the activity of HEK-293 cells expressing GIRK2 alone (FIG. 2b and Table 1b). A similar complete lack of efficacy was observed when VU0456810 was tested on HEK-293 cells expressing GIRK2/3 (Table 1a). Thus, it appears that VU0456810 is only capable of activating GIRK channels containing a GIRK1 subunit. In order to investigate whether VU0456810's activity requires the presence of an active Gi, the effect of pertussis toxin treatment which inactivates ☐i subunits by ADP-ribosylation, was evaluated. As shown in FIG. 2c, in HEK-293 cells co-expressing mGlu8 and GIRK1/2, pertussis toxin treatment was effective at abolishing the ability of glutamate to stimulate an increase in GIRK-mediated thallium flux, while the same treatment was unable to block the effect of VU0456810. In the cell line co-expressing mGlu8 and GIRK1/2, the magnitude of thallium flux evoked by a maximally effective concentration of VU0456810 (10 µM) was approximately twice that evoked by a maximally effective concentration of glutamate (100 µM, FIG. 2c), demonstrating that VU0456810 is a very effective GIRK1/2 activator.

TABLE 1a

Selectivity for VU0456810 for GIRK over other related and unrelated targets. Shown are the data obtain from testing VU0456810 on cells expressing various GIRK subunit combinations. In both thallium flux and whole-cell voltage-clamp experiments VU0456810 displayed robust concentration-dependent efficacy with GIRK1-containing GIRKs and a complete absence of efficacy for GIRKs containing only GIRK2 or GIRK2/3. For thallium flux data, the values represent averages of data from independent experiments ± SEM. For voltage-clamp data, the values represent averages of data from individuals cells across multiple experimental days ± SEM

| Cell Line | EC$_{50}$ Thallium Flux (nM) | N | EC$_{50}$ Voltage Clamp (nM) | N |
|---|---|---|---|---|
| GIRK1-2 | 162 ± 89 | 6 | 584 ± 175 | 9 |
| GIRK1-4 | 887 ± 266 | 3 | 1400 ± 1200 | 9 |
| GIRK1-3 | 914 ± 264 | 4 | Not Determined | 0 |
| GIRK2 | Inactive | 4 | Inactive | 3 |
| GIRK2-3 | Inactive | 3 | Inactive | 3 |

Figure 3:
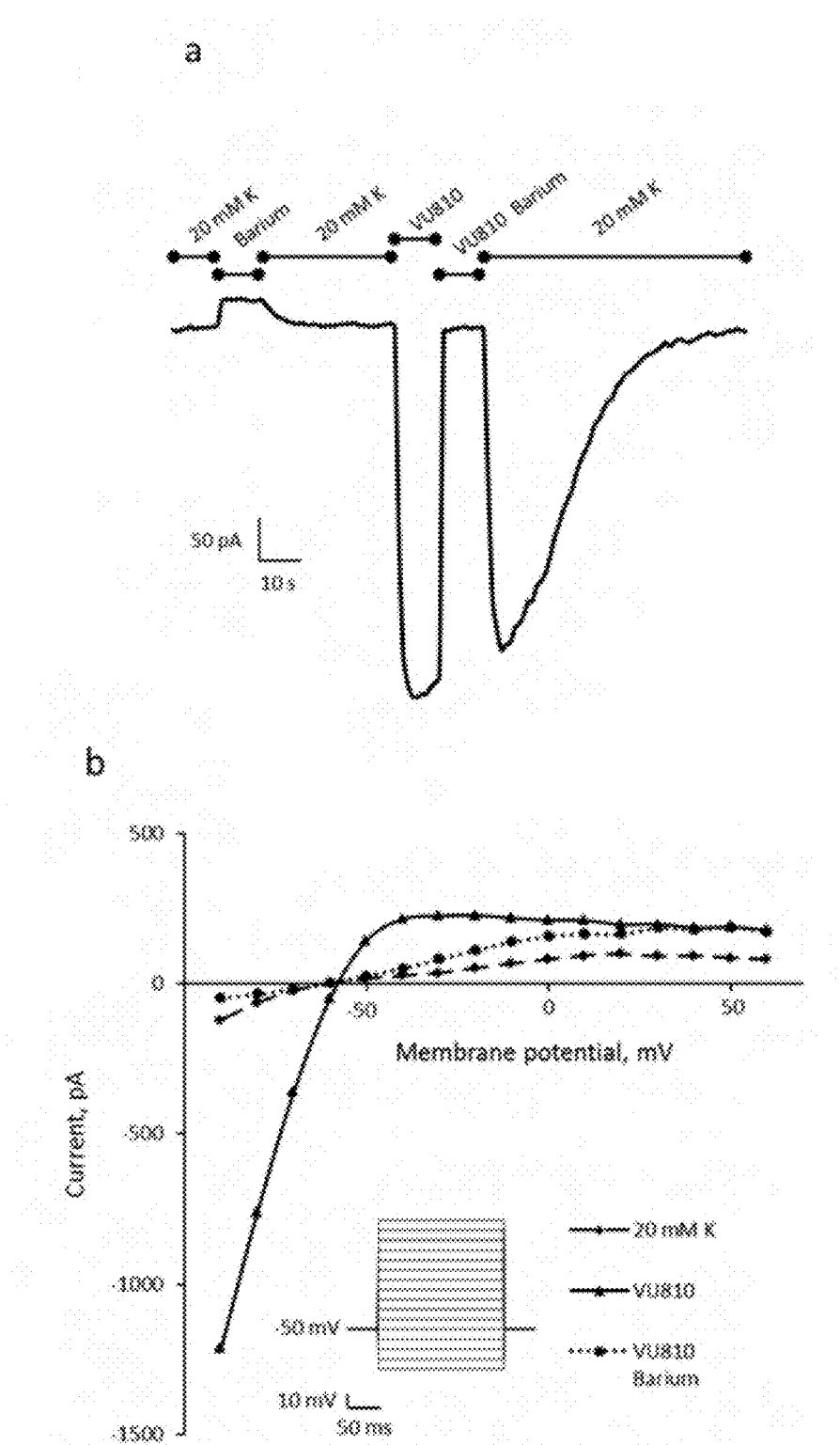
FIG. 3. Electrophysiological Characterization of VU0456810 (VU810). Shown are the results obtained from voltage-clamp experiments performed with VU0456810 on cells expressing GIRK1+GIRK2. a) Representative current traces resulting from treatment of GIRK-expressing cells with 10 μM VU0456810 in the presence of 20 mM extracellular $K^+$. The effect of VU0456810 is inhibited by the addition of the non-selective blocker of inward rectifying potassium channels, Barium (2 mM). b) Current-voltage relationship of currents obtained from GIRK1+GIRK2-expressing cells in the presence and absence of VU0456810 and VU0456810+ Barium (2 mM). All data represent data collected from a minimum of three experiments.

To further explore the findings from thallium flux experiments, the effects of VU0456810 were also studied using whole-cell voltage-clamp in HEK-293 cells expressing GIRK1/2, GIRK1/4, GIRK2 and GIRK2/3. When standard whole-cell voltage clamp was used to evaluate VU0456810, it was found that its activity profile closely matched what was observed with the thallium flux assay (Table 1a) with the compound demonstrating an ability to activate GIRK1/2 and GIRK1/4 but neither GIRK2 nor GIRK2/3. FIG. 3a shows inward currents evoked by the application of VU0456810 to GIRK1/2-expressing HEK-293 cells using a high-speed, local superfusion apparatus. The observed currents were inhibited by the well-known inhibitor of inward-rectifying potassium channels, barium. The onset of current was rapid with 90% of maximal amplitude obtained after approximately 2 seconds of application. However, as illustrated in FIG. 3a, when VU0456810 application was terminated, washout was a slower process requiring nearly a minute. FIG. 3b shows that VU0456810 was able to evoke inward currents that maintained the ion selectivity and inward rectification normally observed with the GIRK channel and (FIG. 3).

To more fully investigate VU0456810's selectivity for GIRK1-containing GIRKs, it was tested using thallium flux assays on cells expressing the closely related potassium channel Kir2.1 as well as two voltage-gated potassium channels, Kv7.4 and hERG. VU0456810 was inactive on Kir2.1 and Kv7.4 and showed a partial ability (~60% at 100 µM) to inhibit the hERG potassium channel with low potency (IC50~10 uM, Table 1b). the selectivity studies on VU0456810 were further extended by submitting VU0456810 to the Lead Profiling (Ricerca, Concord, Ohio) panel of radioligand binding assays. In this panel containing 68 targets, VU0456810 failed to exhibit significant activity at any targets with the exception of modest activity at the 5-HT2b receptor, the sigma 61 receptor, and the GABA$_A$ receptor (muscimol binding site) (Table 1c). Although the levels of binding (<50%) observed at the 10 µM test concentration compared to the potency of VU0456810 at GIRK1-containing GIRKs suggest that these other targets are not likely to be significant concern, it was desirable to rule out the possibility that GABA$_A$ receptor activation or potentiation might confound future behavioral studies. To address this possibility whole-cell voltage-clamp studies were performed on GABA$_A$ receptors (α1, β2, γ2 subunit combination) transiently transfected in HEK-293 cells. In these studies VU0456810 failed to show any activation or potentiation of GABA-evoked currents (Table 1b). Overall, these data suggest that VU0456810 is highly selective for GIRK1-containing GIRK potassium channels and thus represents the first-reported potent, effective, and selective GIRK activator compound.

TABLE 1b

Selectivity for VU0456810 for GIRK over other related and unrelated targets. Shown are the data obtained from testing VU0456810 on cells expressing K$_{ir}$2.1, Kv7.4, hERG using thallium flux assays and GABA$_A$ receptor using whole-cell voltage clamp. VU0456810 showed a complete lack of efficacy on the K$_{ir}$2.1, Kv7.4 and GABA$_A$ receptor-expressing cells and weak partial efficacy on the hERG-expressing cells. The hERG inhibition appeared to plateau at ~60% inhibition where 100% inhibition was defined by that application of a maximally effective concentration of dofetilide. The data represent the average of at least three independent experiments ± SEM

| Cell Line | Potency (µM) | N |
|---|---|---|
| K$_{ir}$2.1 | Inactive | 3 |
| K$_v$7.4 | Inactive | 4 |
| hERG | 10.1 ± 7.0* | 4 |
| GABA$_A$ | Inactive | 3 |

*The maximum inhibition observed was 59.6 ± 8.8% at 100 µM VU0456810

TABLE 1c

Selectivity for VU0456810 for GIRK over other related and unrelated targets. Shown are the results of radioligand-displacement assays performed by Ricerca. Little or no displacement was observed for all but three of the receptors: $GABA_A$ (muscimol binding site), sigma σ1, 5-$HT_{2b}$, which showed a moderate level of displacement.

| Target | Species | Concentration | % Inhibition |
|---|---|---|---|
| Adenosine $A_1$ | human | 10 μM | 6 |
| Adenosine $A_{2A}$ | human | 10 μM | 12 |
| Adenosine $A_3$ | human | 10 μM | 8 |
| Adrenergic $α_{1A}$ | rat | 10 μM | 4 |
| Adrenergic $α_{1B}$ | rat | 10 μM | 1 |
| Adrenergic $α_{1D}$ | human | 10 μM | −3 |
| Adrenergic $α_{2A}$ | human | 10 μM | 4 |
| Adrenergic $β_1$ | human | 10 μM | 0 |
| Adrenergic $β_2$ | human | 10 μM | −5 |
| Androgen | rat | 10 μM | 0 |
| Bradykinin $B_1$ | human | 10 μM | −2 |
| Bradykinin $B_2$ | human | 10 μM | −1 |
| L-Type Ca channel (benzothiazepine) | rat | 10 μM | 1 |
| L-Type Ca channel (dihydropyridine) | rat | 10 μM | 3 |
| N-Type Ca channel | rat | 10 μM | 5 |
| Cannabinoid $CB_1$ | human | 10 μM | 8 |
| Dopamine $D_1$ | human | 10 μM | −5 |
| Dopamine $D_{2s}$ | human | 10 μM | 16 |
| Dopamine $D_3$ | human | 10 μM | 2 |
| Dopamine $D_{4.2}$ | human | 10 μM | 4 |
| Endothelin $ET_A$ | human | 10 μM | 1 |
| Endothelin $ET_B$ | human | 10 μM | 3 |
| EGF | human | 10 μM | −2 |
| Estrogen ERα | human | 10 μM | 1 |
| $GABA_A$ (flunitrazepam) | rat | 10 μM | 24 |
| $GABA_A$ (muscimol) | rat | 10 μM | 49 |
| $GABA_{B1A}$ | human | 10 μM | 11 |
| Glucocorticoid | human | 10 μM | 2 |
| Glutamate (kainate) | rat | 10 μM | 1 |
| Glutamate (NMDA agonism) | rat | 10 μM | 21 |
| Glutamate (NMDA, glycine) | rat | 10 μM | −25 |
| Glutamate (NMDA, PCP) | rat | 10 μM | 1 |
| Histamine $H_1$ | human | 10 μM | −7 |
| Histamine $H_2$ | human | 10 μM | −2 |
| Histamine $H_3$ | human | 10 μM | 1 |
| Imidazoline, I2 | rat | 10 μM | 20 |
| Interleukin IL-1 | mouse | 10 μM | 2 |
| Leukotriene | human | 10 μM | 4 |
| Melatonin $MT_1$ | human | 10 μM | 11 |
| Muscarinic $M_1$ | human | 10 μM | 0 |
| Muscarinic $M_2$ | human | 10 μM | −17 |
| Muscarinic $M_3$ | human | 10 μM | 13 |
| Neuropeptide Y (Y1) | human | 10 μM | 24 |
| Neuropeptide Y (Y2) | human | 10 μM | −5 |
| Nicotinic acetylcholine | human | 10 μM | 0 |
| Nicotinic acetylcholine | human | 10 μM | 7 |
| Opiate (DOP) | human | 10 μM | −4 |
| Opiate (KOP) | human | 10 μM | 1 |
| Opiate (MOP) | human | 10 μM | 21 |
| Phorbol ester | mouse | 10 μM | 1 |
| PAF | human | 10 μM | 2 |
| Potassium channel $K_{ATP}$ | human | 10 μM | 2 |
| Potassium channel hERG | human | 10 μM | 10 |
| Prostanoid $EP_4$ | human | 10 μM | −4 |
| Purinergic $P_{2X}$ | rabbit | 10 μM | 16 |
| Purinergic $P_{2Y}$ | rat | 10 μM | 4 |
| Rolipram (PDE4) | human | 10 μM | 11 |
| Serotonin 5-$HT_{1A}$ | human | 10 μM | 0 |
| Serotonin 5-$HT_{2B}$ | human | 10 μM | 46 |
| Serotonin 5-$HT_{2b}$ | human | 10 μM | 1 |
| Sigma σ1 | human | 10 μM | 49 |
| Tachykinin $NK_1$ | human | 10 μM | 3 |
| Thyroid hormone | human | 10 μM | 8 |
| Transporter, DAT | human | 10 μM | 12 |
| Transporter, GABA | rat | 10 μM | 5 |
| Transporter, NET | human | 10 μM | 15 |
| Transporter, SERT | human | 10 μM | −1 |

To investigate the pharmacological properties of VU0456810 and to explore its value as a tool for understanding a GIRK activator's potential for therapeutic benefit, tests were conducted to begin to explore the behavioral effects of the compound administered to rodents in vivo. Prior to conducting these studies, a number of in vitro and in vivo pharmacokinetic assays were performed to assess VU0456810's suitability as an in vivo tool. VU0456810 showed good solubility (17.5 μM), modest protein binding (3% $f_u$) in murine plasma, and moderate stability in murine liver microsomes ($rCl_{HEP}$=88 mL/min/kg, Table 2). When VU0456810 was administered by intraperitoneal injection into mouse, moderately-rapid clearance was observed with a half-life of 20 minutes and a moderate brain penetration (brain (0.5 μM): plasma (2.3 μM) ratio of 0.2 at 30 min after administration, Table 2). These features of VU0456810 suggested that it, while sub-optimal with respect to free-fraction, half-life, and brain penetration, may possess suitable properties for pharmacodynamic studies.

TABLE 2

Murine in vitro and in vivo DMPK data for VU0456810. Shown are data from in vitro and in vivo obtained from tests with VU0456810. In vitro data: solubility, plasma protein binding, and microsomal clearance, represent averages of a minimum of three replicates. In vivo data: brain and plasma concentrations, represent the average data from three animals after intraperitoneal injection of a 10 mg/kg dose.

| Assay | Result |
|---|---|
| Plasma Protein Binding | 3% $f_u$ |
| Solubility | 17.5 μM |
| Microsomal Clearance | 88 ml/min/kg |
| In vivo half-life | 20 minutes |
| Brain concentration | 0.5 μM |
| Plasma concentration | 2.3 μM |
| Brain/Plasma | 0.2 |

Figure 5:
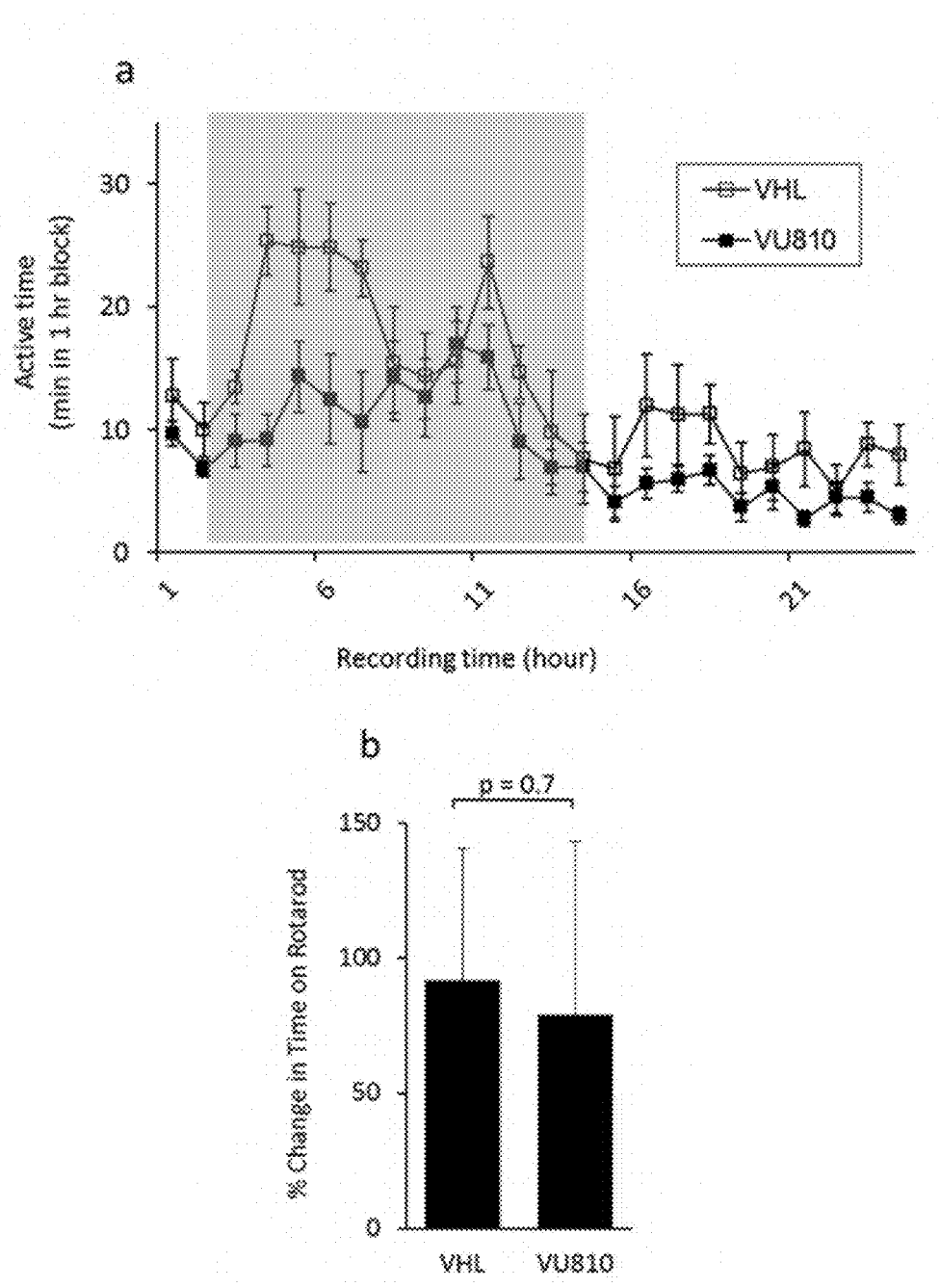
FIG. 5. Effects in vivo administration of VU0456810 (VU810) on activity levels and motor function. Shown in (a) are the effects of VU0456810 on the activity level of mice (n=6) in their home cage recorded using a SmartCage device. Overall activity levels are decreased in the VU0456810-treated compared to the vehicle control-treated group. The shaded area represents the time the animals cages were in the dark phase. Shown in (b) are the data resulting from testing mice (n=6) treated with VU0456810 on a rotarod apparatus. The VU0456810 animals showed a small and insignificant decrease in rotarod performance compared to the vehicle-treated controls.

To begin to assess VU04546810's pharmacodynamics properties, an ascending dose study (10, 30, 60 mg/kg, intraperitoneal injection) was performed in mice. At all doses tested, the animals appeared normal and not under obvious distress. Then, VU0456810's effects on locomotor activity as well as effects on motor function and coordination were more thoroughly examined. As a general test of locomotor activity, the activity of VU0456810 (60 mg/kg) and vehicle treated animals in their home cages for 24 hours after injection was assessed. In the VU0456810-treated animals, an overall decrease in locomotor activity over the 24 hour period was noted compared to the control group with differences being most pronounced in the dark phase of testing when mice are typically most active (FIG. 5a). As a test of VU0456810's effects on motor function and coordination, mice treated with a 60 mg/kg dose of VU0456810 were examined using a rotarod apparatus. When compared to the vehicle-treated animals, the VU0456810-treated group showed a modest (14%) but insignificant (p=0.7) decrease in performance on the rotarod (FIG. 5b).

Figure 4:
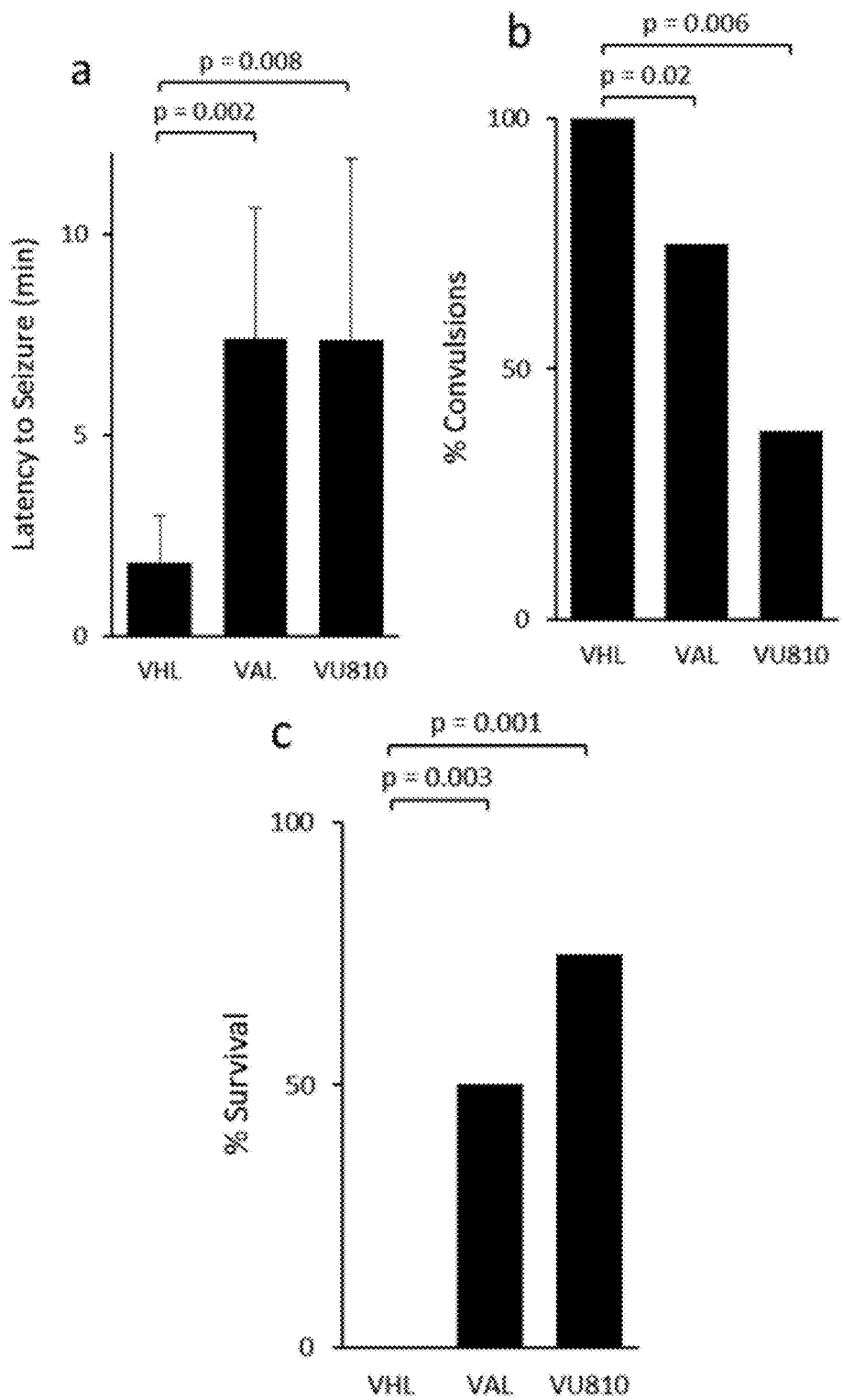
FIG. 4. VU0456810 (VU810) is active in two models of epilepsy. Shown are data obtained from mice after intraperitoneal dosing with VU0456810 (60 mg/kg) or sodium valproate (150 mg/kg). In (a) are the measured latencies before seizure onset in mice exposed to a lethal electrical shock. Both the antiepileptic positive control, sodium valproate (VAL), and VU0456810 showed highly significant delays in seizure onset. In (b) and (c) are the data obtained from mice injected with the $GABA_A$ inhibitor, PTZ. Shown in (b) are the percentage of animals tested that experienced convulsions from PTZ treatment and in (c) the percentage of animals that survived PTZ treatment. In both cases VAL and VU0456810 showed a significant decrease in the number of animals experiencing convulsions and a significant increase in the number of animals surviving PTZ treatment compared to vehicle (VHL)-treated controls.

Following locomotor activity and motor coordination tests, VU0456810 was evaluated in a maximal electroshock (MES) model of epilepsy in mice. At the 60 mg/kg dose a robust increase was observed in the latency of seizure onset equivalent to that observed with a 150 mg/kg dose of the known anti-epileptic, sodium valproate (FIG. 4a). Both the effects of VU0456810 and sodium valproate were highly significant compared to vehicle-treated animals with measured p-values of 0.008 and 0.002, respectively. Upon achieving activity in the MES model, the efficacy of the 60 mg/kg dose of VU0456810 was investigated in a chemically induced epilepsy model. In this model, the GABAA antagonist pentylenetetrazol (PTZ) was administered to induce seizures after administration of VU0456810 (60 mg/kg), sodium valproate (150 mg/kg), or vehicle. As in the MES model, both sodium valproate and VU0456810 were effective when compared to the vehicle control (FIG. 4 b,c). VU0456810 showed a highly significant ability to both prevent convulsions (p=0.006) and prevent fatality of the PTZ treatment (p=0.001) with most of the animals treated with VU0456810 neither experiencing convulsions (5 out of 8 animals did not experience convulsions compared to 15 out of 15 in the control group) nor death (6 out of 8 animals survived the treatment compared to 15 out of 15 in the control group) within the 20 minute timeframe of the testing procedure.

Discussion

Although the GIRK family of potassium channels has been of intense research interest for nearly two decades, selective pharmacological tools have remained elusive. In particular, the lack of selective and potent GIRK activators has prevented investigators from probing the effects of selective GIRK activation in normal and pathophysiological conditions, as well as potential adverse effects induced by GIRK activation. In the present study, the discovery and characterization of the first highly potent, selective, in vivo-active GIRK activator, VU0456810, is reported and intriguing data is provided that implicates GIRK as a novel target for the treatment of epilepsy. Unlike the activation of GIRK mediated through Gi-couple GPCRs, it was found that VU0456810's effects were immune to inhibition by pertussis toxin. These data support the suggestion that VU0456810 works via direct action at the GIRK channel and does not require the presence of activated Gi GPCRs. It was also found that VU0456810 displays a surprising preference for GIRK channels that contain the GIRK1 subunit. When VU0456810 was tested on GIRKs that did not contain GIRK1, activity was note detected at any concentration tested whether using the thallium flux assay or standard whole-cell patch clamp. In contrast, VU0456810 displayed efficacy on every GIRK1-containing GIRK channel that was tested, including GIRK1/2, GIRK1/3, and GIRK1/4. Furthermore, none of the compounds related to VU0456810 that were synthesized as part of VU0456810's development showed any activity at non-GIRK1-containing GIRKs, regardless of their activity at GIRK1-containing channels. These observations support the hypothesis that at least a portion of the binding site for VU0456810 is unique to GIRK1. It is tempting to speculate that this binding site could be contributed, at least in part, by the carboxy-terminal tail extension that is unique to GIRK1. This tail is reported to have effects on GIRK regulation26 and future studies will focus on the elucidation of the binding site for VU0456810. The fact that VU0456810's efficacy is limited to GIRK1-containing GIRK channels provides an excellent opportunity to begin to address questions about the roles of GIRK1 and non-GIRK1-containing GIRKs. The ability to target specific GIRK subunit combinations may also provide a basis to selectively modulate certain physiological pathways and not others, which could have important benefits when considering therapeutic uses for GIRK modulators.

To begin to explore the potential for GIRK activators as in vivo tools and potential therapeutic targets, the effects of systemic administration of VU0456810 in mice was investigated. VU0456810 injected animals appeared normal, and without any notable behavioral effects, immediately after injection. However, continued observation under home cage conditions using the SmartCage™ system28 revealed a modest decrease in general locomotor activity, predominantly during the dark phase. Importantly, when the effects of VU0456810 on motor function and coordination were assessed using a rotarod, significant effects were not observed. Thus, VU0456810's effects on generalized locomotor activity do not appear to be through compound-induced motor deficits but instead may be mediated through increased sleep time. Future studies will focus on increasing the understanding of the mechanism by which VU0456810 produces the observed decreases in locomotion.

Previous development of GIRK2 knockout animals has revealed an epilepsy phenotype, suggesting a role for GIRK in regulating excitability.27 The present inventors contemplated that, because the GIRK1/2 subunit combination is most prevalent in the brain, a GIRK1/2 activator might produce effects in an epilepsy model in vivo. Despite the fact that VU0456810's DMPK properties were sub-optimal with a relatively short half-life, modest free-fraction, and modest brain penetration, robust activity was observed in two epilepsy models. Regardless of whether epilepsy was initiated chemically with PTZ or via electroshock, VU0456810 showed equal or greater efficacy compared to a clinically active anti-seizure medication, sodium valproate. These data support a role for selective GIRK activation in controlling excitability and provide the first evidence for the exciting possibility that GIRK may, in fact, represent an attractive new target for antiepileptic drugs. The recent registration of the KCNQ positive modulator, retigabine (Potiga), provides a concrete example for selectively targeting potassium channel activation as a means of treating epilepsy.

This study is the first to describe SAR related to selective GIRK activation, and a multi-dimensional iterative library approach rapidly identified a potent and highly efficacious GIRK channel activator, VU0456810. Overall, SAR within the VU810 series was very robust and of considerable texture. As shown in FIG. 1, the urea linkage and the N-phenylpyrazole appear to be useful for GIRK activity, while a range of substituted aryl moieties are tolerated on the western urea NH. In general, halogen substitution in the 3- or 3,4-positions of the western aryl ring proved optimal for both GIRK1/2 potency and efficacy. Metabolite identification studies suggest the 3-methyl moiety on the pyrazole is the site for CYP-mediated oxidation, and a site for further chemical optimization. While VU0456810 shows exquisite selectivity when considering GIRK1 vs non-GIRK1-containing GIRKs, it only shows a modest preference for the activation of the GIRK1/2 subunit combination vs GIRK1/3 or GIRK1/4, with measured potencies all within a 6-fold range. SAR developed thus far in the VU810 scaffold, coupled with metabolite identification studies, suggest a pathway forward in this chemotype to improve GIRK1/2 selectivity while improving CNS exposure; moreover, ongoing medicinal chemistry efforts will focus on development of additional probes with improved selectivity for the different GIRK1 subunit combinations. VU0456810 and other more selective probes will provide a basis to begin to probe GIRK1-containing GIRKs roles and therapeutic potential in a variety of other indications including anxiety, pain, feeding, and addiction/withdrawal. Taken together, the data provide the first demonstration of the discovery, improvement, and characterization of a potent, selective, in vivo-active GIRK activator, paving the way for a more complete understanding of GIRKs' role in physiology as well as the exploration of its potential for a wide range of therapeutic indications. The data also point to key structural differences in GIRK1 and non-GIRK1 containing GIRKs, which may lead to new insights into GIRK structure, function, and regulation.

Methods

Compound Synthesis

All reagents were purchased from Sigma-Aldrich Corp., TCI America, and Rieke Metals, Inc. and were used without purification. All polymer supported reagents were purchased from Biotage, Inc. Analytical thin-layer chromatography (TLC) was performed on 250 μm silica gel plates from Sorbent Technologies. Visualization was accomplished via UV light, and/or the use of ninhydrin and potassium permanganate solutions followed by application of heat. Chromatography was performed using Silica Gel 60 (230-400 mesh) from Sorbent Technologies or Silica RediSep Rf flash columns on a CombiFlash Rf automated flash chromatography system. All 1H, 13C and 19F NMR spectra were recorded on a Bruker AV-400 (400 MHz) instrument. Chemical shifts are reported in ppm relative to residual solvent peaks as an internal standard set to δ 7.26 and δ 77.16 (CDCl3). Data are reported as follows: chemical shift, multiplicity (s=singlet, d=doublet, t=triplet, q=quartet, p=pentet br=broad, dd=doublet of doublets, dq=doublet of quartets, td=triplet of doublets, pd=pentet of doublets, m=multiplet), coupling constant (Hz), integration. Low resolution mass spectra (LCMS) were obtained on an Agilent 1200 LCMS with electrospray ionization. High resolution mass spectra (HRMS) were recorded on a Waters Qtof-API-US plus Acquity system with ES as the ion source. Analytical high pressure liquid chromatography (HPLC) was performed on an Agilent 1200 analytical LCMS with UV detection at 214 nm and 254 nm along with ELSD detection.

1-(3,4-difluorophenyl)-3-(3-methyl-1-phenyl-1H-pyrazol-5-yl)urea (VU0456810)—To a solution of 3-methyl-1-phenyl-1H-pyrazol-5-amine (500 mg, 2.9 mmol) in 11.5 ml of CH2Cl2 was added 3,4-difluorophenylisocyanate (0.68 ml, 5.8 mmol). After 16 h the reaction was concentrated and the residue was purified by column chromatography with MeOH/CH2Cl2 to afford 418 mg (65%) of the desired product. 1H NMR (MeOD) ☐ 7.50 (m, 6H), 7.13 (dd, J=19.2, 9.6 Hz, 1H), 6.98 (m, 1H), 6.35 (s, 1H), 2.27 (s, 3H); 13C NMR (MeOD) ☐ 152.3, 149.8 (dd, J=13.2, 242.9 Hz), 149.1, 145.8 (dd, J=12.8, 240.4 Hz), 137.7 (d, 13.1 Hz), 135.6 (dd, J=2.9, 9.0 Hz), 129.2, 128.1, 125.0, 116.7 (d, J=18.1), 114.5 (dd, 3.6, 5.7 Hz), 107.9 (d, J=21.8 Hz), 98.4, 12.2; 19F NMR (MeOD) ☐ −137.3 (d, J=22.6 Hz), −145.9 (d, J=22.6 Hz); HRMS calculated for C17H14F2N4O (M+H)+m/z: 329.1214. Measured 329.1211 m/z.

Cell Line Construction and Cell Culture. HEK-293 cells co-expressing human GIRK1/2 and rat mGlu8 were generated as previously described (Niswender et al., 2008). A HEK-293 cell line (ATCC, Manassas, Va.) expressing human GIRK1 and human GIRK2 was constructed by transfecting HEK-293 cells with GIRK1 and GIRK2 (Origene, Rockville, Md.) cloned into the pBudCE4.1 vector (Life Technologies, Carlsbad, Calif.) using FuGene 6 (Promega, Madison, Wis.) transfection reagent. Unless otherwise noted, other ion channel-expressing cells were prepared by transfecting HEK-293 cells with individual or combinations of subunits: GIRK1, pCMV6-A-BSD; GIRK2, pCMV6-A-puro; GIRK3, pCMV6-A-hygro; GIRK4, pCMV6-A-AC; Kv7.4, pIRESneo3. The Kir2.1 and hERG-expressing cell lines were made by transfecting T-REx-293 cells (Life Technologies, Carlsbad, Calif.) with Kir2.1 and Kv11.1, respectively, cloned into pcDNA5TO. Monoclonal cell lines were produced by limiting-dilution cloning of antibiotic-resistant cells and functional selection using the thallium flux assay described below. Unless otherwise noted, cells were maintained in Minimal Essential Medium, Alpha Medium (Mediatech, Manassas, Va.) supplemented with 10% fetal bovine serum (Sigma-Aldrich, Saint Louis, Mo.) and GlutaGro (Mediatech, Manassas, Va.), referred to henceforth as cell culture medium. Cell culture medium was further supplemented with selection antibiotics, as appropriate.

Thallium Flux Assays

For thallium flux assays, cells were dislodged from tissue culture flasks using TrypLE Express (Life Technologies, Carlsbad, Calif.), transferred to a 50 mL centrifuge tube, and spun at 500×g for 2 min. The supernatant solution was removed by aspiration and the pellet was resuspended at concentration of ~1000 cells/μL. Twenty μL/well of the cell suspension was transferred to 384-well, amine-coated assay plates (cat#354719, BD, Franklin Lakes, N.J.) using an electronic multichannel pipette. Plated cells were incubated overnight in a humidified 5% CO2 cell culture incubator at 37° C. After overnight incubation the cell culture medium was replaced with 20 μL/well of a dye loading solution containing assay buffer (Hanks Balanced Salt Solution plus 20 mM HEPES, pH 7.3), 0.04% (w/v) Pluronic F-127 (Sigma-Aldrich, St. Louis, Mo.), and 1.2 μM of the thallium-sensitive dye Thallos-AM (Teflabs, Austin, Tex.). Following a ~1 hour incubation at room temperature, the dye loading solution was replaced with 20 μL/well assay buffer and the plates were loaded into a Hamamatsu FDSS 6000 (Bridgewater, N.J.). Data were acquired at 1 Hz (excitation 470+/−20 nm, emission 540+/−30 nm) for ten seconds, followed by the addition of 20 μL/well of test compounds (prepared as described below), followed by an additional 4 min of data collection. At the 4 min mark, 10 μL/well of a thallium stimulus buffer was added and data collection continued for an additional 2 min. The thallium stimulus buffer contained (in mM) 125 NaHCO3, 1.8 CaSO4, 1 MgSO4, 5 glucose, 2.4 Tl2SO4, 10 mM HEPES pH 7.4.

For the thallium flux assay of the GIRK1+GIRK3 containing cell line, the Tl2SO4 concentration in the stimulus buffer was 12 mM. For the thallium flux assays of hERG a modified assay buffer was used for test compound dilution where 60 mM of the NaCl was replaced with 60 mM KCl (High-K+ assay buffer). Additionally, for the hERG assay, the time of incubation with compound prior to thallium stimulus buffer addition was 20 min. For experiments with pertussis toxin, cells expressing GIRK1+GIRK2+mGlu8 were plated and assays conducted as for other thallium flux assays with the following exception: after overnight incubation of plated cells in a humidified 5% CO2 cell culture incubator at 37° C., the cell culture medium was replaced with 20 μL/well cell culture medium containing 600 ng/ml pertussis toxin (Tocris, Bristol, UK). Plates containing pertussis toxin were returned to the cell culture incubator for 8 hours after which time the cell culture medium was removed and the assays conducted as described above for other thallium flux assays with the addition of varying concentrations of glutamate to the thallium stimulus buffer for the activation of the mGlu8 receptor co-expressed with GIRK1+GIRK2.

Compounds were dissolved in neat DMSO to a concentration of 30 mM-100 mM. Forty-five microliter aliquots were placed in 384-well, flat-bottom, Echo-qualified, poly-propylene plates (Labcyte, Sunnyvale, Calif.). Samples were diluted in 3-fold steps in DMSO using a Bravo liquid handler (Agilent, Santa Clara, Calif.) with tip changes between each dilution step. Serially diluted samples were transferred to 384-well, round-bottom, polypropylene plates (Greiner, Monroe, N.C.) using an Echo555 plate reformatter (Labcyte, Sunnyvale, Calif.). Samples were then diluted with assay buffer using a Combi (Thermo Fisher, Waltham, Mass.) and mixed vigorously. Diluted samples were used within an hour of dilution. Final DMSO concentrations in all studies were 0.3% or less.

Thallium flux data were analyzed in Excel (Microsoft, Redmond, Wash.) by first dividing each point in each wave by the first point in that wave (F/F0) and then subtracting the average of the vehicle control waves from each wave. The slopes of these vehicle control-subtracted waves was calculated from ten data points beginning 2 seconds after thallium stimulus addition. Slope values were used to obtain fits to a four parameter logistic equation in XLfit (IDBS, Guildford, Surrey, UK).

Electrophysiology

For whole-cell, voltage-clamp assays, compound were diluted into DMSO stocks in 20 mM KCl, 140 mM NaCl, 0.5 mM CaCl2, 2 mM MgCl2 and 10 mM HEPES (pH 7.4), referred to hereafter as 20K Extracellular Solution. The GIRK activator probe, VU0456810, was serially diluted in DMSO manually from a 100 mM DMSO stock further diluted to make test samples in 20K extracellular solution.

A single-cell suspension of HEK-293 cells stably transfected with the appropriate ion channels were plated into TC-treated 35 mm polystyrene dishes at ~15% confluence and incubated overnight in a 5% CO2 cell culture incubator at 37° C. Whole-cell patch-clamp recordings were performed 24-72 h after plating. Borosilicate glass electrodes (5-7 m resistance) were filled with Intracellular Solution (130 mM KCl, 20 mM NaCl, 5 mM EGTA, 5.46 mM MgCl2, and 10 mM HEPES, pH 7.4). Whole cell currents were recorded in 20K extracellular solution at −70 mV using a Pico 1 amplifier (Tecella, Foothill Ranch, Calif.) controlled by WINWCP 4.X (University of Strathclyde, Glasgow, Scotland, UK). Signals were compensated for electrode capacitance, cellular capacitance and series resistance. Signals were filtered at 1 kHz, and digitized at 5 kHz. Solutions were applied to the cell with a Valvelink 8.2 (Automate Scientific, Berkeley, Calif.) rapid, valve-controlled perfusion system with in-house-made local superfusion manifold. Barium-sensitive currents measurements were obtained by applying the non-selective Kir inhibitor, 2 mM BaCl2, in 20K extracellular solution in the absence and presence of test compounds and measuring the amplitude of the Ba2+-sensitive current. For testing activity of VU0456801 on GABAA receptors, HEK-293 cells were transiently transfected with GABAA subunits □1, □2, □2 using Fugene 6 (Promega, Madison, Wis.)). One day after transfection, cells were plate into 35 mm polystyrene dishes, incubated and recorded as described above. For GABAA receptor potentiation studies VU0456801 was added in the presence of 3 μM GABA.

Voltage-clamp data were analyzed by converting current amplitudes to current density by dividing by each cell's membrane capacitance estimated from capacitance compensation. For concentration-response experiments, barium-sensitive, steady-state currents density values obtained at different compound concentrations were fit using a four-parameter logistic equation in XLfit.

DMPK Methods. In vitro: The metabolism of VU0456810 was investigated in rat, mouse, and human hepatic microsomes (BD Biosciences) using substrate depletion methodology (% test article remaining). hepatic microsomes (0.5 mg/mL) and 1 μM test compound were incubated in 100 mM potassium phosphate pH 7.4 buffer with 3 mM MgCl2 at 37° C. with constant shaking. After a 5 min preincubation, the reaction was initiated by addition of NADPH (1 mM). At selected time intervals (0, 3, 7, 15, 25, and 45 min), 50 μL aliquots were taken and subsequently placed into a 96-well plate containing 150 μL of cold acetonitrile with internal standard (50 ng/mL carbamazepine). Plates were then centrifuged at 3000 rcf (4° C.) for 10 min, and the supernatant was transferred to a separate 96-well plate and diluted 1:1 with water for LC/MS/MS analysis. The in vitro half-life ($T_{1/2}$, min, Eq. 1), intrinsic clearance ($CL_{int}$, mL/min/kg, Eq. 2) and subsequent predicted hepatic clearance ($CL_{hep}$, mL/min/kg, Eq. 3) were determined employing the following equations:

$$T_{1/2} = \frac{Ln(2)}{k} \quad (1)$$

where k represents the slope from linear regression analysis of the natural log percent remaining of test compound as a function of incubation time $$CL_{int} = \frac{0.693}{\text{in vitro } T_{1/2}} \times \frac{\text{mL incubation}}{\text{mg microsomes}} \times \frac{45 \text{ mg microsomes}}{\text{gram liver}} \times \frac{20^a \text{ gram liver}}{\text{kg body wt}} \quad (2)$$

$^a$scale-up factors: of 20 (human), 45 (rat), or 87.5 (mouse)

$$CL_{hep} = \frac{Q_h \cdot CL_{int}}{Q_h + CL_{int}} \quad (3)$$

where $Q_h$ (hepatic blood flow, mL/min/kg) is 21 (human), 70 (rat), or 90 (mouse).

Plasma Protein Binding. Protein binding of VU0456810 was determined in plasma via equilibrium dialysis employing Single-Use RED Plates with inserts (ThermoFisher Scientific). Briefly plasma (220 μL) was added to the 96-well plate containing test article (5 μL) and mixed thoroughly. Subsequently, 200 μl of the plasma-test article mixture was transferred to the cis chamber (red) of the RED plate, with an accompanying 350 μL of phosphate buffer (25 mM, pH 7.4) in the trans chamber. The RED plate was sealed and incubated 4 h at 37° C. with shaking. At completion, 50 μL aliquots from each chamber were diluted 1:1 (50 μL) with either plasma (cis) or buffer (trans) and transferred to a new 96-well plate, at which time ice-cold acetonitrile (2 volumes) was added to extract the matrices. The plate was centrifuged (3000 rcf, 10 min) and supernatant solutions transferred to a new 96-well plate. The sealed plate was stored at −20° C. until LC/MS/MS analysis.

Liquid Chromatography/Mass Spectrometry Analysis. In vitro experiments. VU0456810 was analyzed on a Thermo Electron TSQ Quantum Ultra triple quad mass spectrometer (San Jose, Calif.) via electrospray ionization (ESI) with two Themo Electron Accella pumps (San Jose, Calif.), and a Leap Technologies CTC PAL autosampler (Carrboro, N.C.). Analytes were separated by gradient elution on a dual column system with two Thermo Hypersil Gold (2.1×30 mm, 1.9 µm) columns (San Jose, Calif.) at 40° C. HPLC mobile phase A was 0.1% formic acid in water and mobile phase B was 0.1% formic acid in acetonitrile. The gradient started at 10% B after a 0.2 min hold and was linearly increased to 95% B over 0.8 min; hold at 95% B for 0.2 min; returned to 10% B in 0.1 min. The total run time was 1.3 min and the HPLC flow rate was 0.8 mL/min. While pump 1 ran the gradient method, pump 2 equilibrated the alternate column isocratically at 10% B. Compound optimization, data collection and processing were performed using Thermo Electron's QuickQuan software (v2.3) and Xcalibur (v2.0.7 SP1).

In Vivo Pharmacokinetic Study. Compound(s) were formulated in 10% Tween80 in sterile water at the concentration of 3.33 mg/mL and administered IP to male C57 BL6 mice weighing 20 to 25 g (Harlan, Indianapolis, Ind.) at the dose of 10 mg/kg. The blood (cardiac puncture) and brain were collected at 0.5, 1, 3, and 6 hr. Animals were euthanized and decapitated, and the brains were removed, thoroughly washed in cold phosphate-buffered saline, and immediately frozen on dry ice. Plasma was separated by centrifugation (4000 rcf, 4° C.) and stored at −80° C. until analysis. On the day of analysis, frozen whole-rat brains were weighed and diluted with 1:3 (w/w) parts of 70:30 isopropanol:water. The mixture was then subjected to mechanical homogenation employing a Mini-Beadbeater™ and 1.0 mm Zirconia/Silica Beads (Bio-Spec Products) followed by centrifugation. The sample extraction of plasma (20 µL) or brain homogenate (20 µL) was performed by a method based on protein precipitation using three volumes of ice-cold acetonitrile containing an internal standard (50 ng/mL carbamazepine). The samples were centrifuged (3000 rcf, 5 min) and supernatants transferred and diluted 1:1 (supernatant: water) into a new 96 well plate, which was then sealed in preparation for LC/MS/MS analysis.

LC/MS/MS Bioanalysis of Samples from In Vivo Studies. In vivo samples were analyzed via electrospray ionization (ESI) on an AB Sciex QTrap 5500 (Foster City, Calif.) triple-quadrupole linear ion trap instrument that was coupled with Shimadzu LC-20AD pumps (Columbia, Md.) and a Leap Technologies CTC PAL auto-sampler (Carrboro, N.C.). Analytes were separated by gradient elution using a Fortis C18 2.1×50 mm, 3 µm column (Fortis Technologies Ltd, Cheshire, UK) at 40° C. HPLC mobile phase A was 0.1% formic acid in water (pH unadjusted), mobile phase B was 0.1% formic acid in acetonitrile (pH unadjusted). The gradient started at 30% B after a 0.2 min hold and was linearly increased to 95% B over 0.6 min; held at 90% B for 0.7 min and returned to 10% B in 0.1 min followed by a re-equilibration (0.9 min). The total run time was 2.5 min and the HPLC flow rate was 0.5 mL/min. The source temperature was set at 500° C. and mass spectral analyses were performed using multiple reaction monitoring (MRM), with transitions specific for each compound utilizing a Turbo-Ionspray® source in positive ionization mode (5.0 kV spray voltage). The calibration curves were constructed, and linear response was obtained in the range of 0.5 to 5,000 ng/mL, by spiking known amounts of VU0465810 in blank brain homogenate or plasma. All data were analyzed using AB Sciex Analyst software v1.5.1. The final PK parameters were calculated by noncompartmental analysis using Phoenix (version 6.2) (Pharsight Inc., Mountain View, Calif.).

In Vivo Pharmacology Assays

For the pentylenetetrazol (PTZ)-induced seizure model, male mice (C57/BL6, 8-10 months old, approximately 30 g) were injected intraperitoneally with either VU0456810 (60 mg/kg), sodium valproate (150 mg/kg) or vehicle (2% DMSO in 0.5% aqueous hydroxypropyl cellulose). After thirty minutes, PTZ was administered intraperitoneally (i.p., 40 mg/kg). Immediately following administration of PTZ, the amount of time elapsed before the first occurrence of tremors, tonic-clonic seizures, convulsion, and death was recorded. All mice were subject to a 20-minute post-STZ cutoff. If a mouse did not reach death after 20 min post-STZ, the mouse was euthanized by isoflurane inhalation. The average fatality latencies (in minutes) and the fatality rates of the VU0456810 group, the sodium valproate group, and the vehicle group were compared (n=8 mice/group).

For the maximal electroshock seizure (MES) model, male, C57/BL6 mice (8-10 months old, approximately 30 g), were injected intraperitoneally with either VU0456810 (60 mg/kg), sodium valproate (150 mg/kg) or vehicle. MES stimulation was applied, 30 minutes after injection, through transauricular (ear-clip) electrodes from an electroshock apparatus, HSE Shock Stimulator Type 221, (Harvard Apparatus, Holliston, Mass.) using the following parameters: 100-mA fixed current, a 50-60-Hz pulse frequency, a 0.6-ms pulse width and a 0.3-s stimulus duration. Animals were restrained by hand when applying the electrodes and released at the moment of stimulation to permit observation of the seizure throughout its entire course. Upon completion of the electrical stimulus, the amount of time until death was recorded. A 10-minute cutoff was applied to all mice; mice that did not reach fatality within 10 minutes were euthanized by isoflurane inhalation. In this modified MES test, the electrical stimulus that was applied was sufficient to induce seizures and death from maximal seizure in 100% of the control mice.

In all cases, experiments were conducted in a blind manner with respect to the experimenters. Data were evaluated in Excel using one-tailed, unpaired Student's t-test, assuming populations with unequal variance.

In Vivo Pharmacology

The SmartCage™ system (AfaSci, Inc., Burlingame, Calif.) was used to assess compound effects on spontaneous homecage activity. Automated data analysis was performed using CageScore™ software (AfaSci, Inc.). The home cage activity was determined by beam breaks (x, y, and z photobeam break counts). Distance traveled in centimeters was obtained from the lower horizontal sensors (x and y) taking into account the path taken. Average velocity was distance traveled/second in the forward direction, averaged over the block time (bin). Mice (male C57/BL6, 8-10 months old, approximately 30 g) mice were assessed continuously for 72 hours. The first 24 hours was used as a habituation period. The locomotion data obtained from the second 24 hours served as the baseline data for each mouse. At the completion of the second 24 hours, each mouse was injected intraperitoneally with either VU0456810 (60 mg/kg) or vehicle (2% DMSO in 0.5% aqueous hydroxypropyl cellulose). After receiving their respective treatments, each mouse's locomotor activity was monitored over the 24 hours to assess recovery from drug effects.

For rotarod tests, a rotarod module was inserted into a mouse home cage and was operated by the SmartCage™ (AfaSci, Inc., Redwood City, Calif.) system28. A mouse was placed on the rod and the rod began to rotate at a fixed speed (15 rpm). Latencies for the mice to fall off the rod were recorded. Mice that did not fall off the rod after 10 minutes were manually removed from the rod. Two groups of mice (n=8 mice/group) were trained on the rotarod over 4 consecutive days. On training days, each mouse was allowed to perform on the rotarod a total of 4 times. For each training day, each mouse's lowest rotarod latency was excluded. The remaining 3 rotarod latencies were averaged and served as the mouse's rotarod performance for that training day. Upon completion of training on day 4, one group received an intraperitoneal injection of VU0456810 (60 mg/kg), whereas the other group received the vehicle. Approximately 1 hour post-drug/vehicle injection, each mouse's rotarod performance was assessed a total of 4 times with the mouse's worst performance being excluded. The remaining 3 rotarod latencies were then averaged for each mouse and these values were normalized to the mouse's previous performance on the final training day to account for variation in individual animal's competency on the rotarod.

Example 2

The G protein regulated Inwardly Rectifying Potassium (K+) (GIRK) channels are a family of inward-rectifying potassium channels also known as the Kir3 family, whose physiological role is to modulate the excitability of the various cell types in which they are expressed. Kubo, (1993), Lesage (1994), Kobayashi (1995), Karschin (1996) Four GIRK channel subunits are expressed, as either homo- or heterodimers, in mammals: GIRK1 (Kir3.1), GIRK2 (Kir3.2), GIRK3 (Kir3.3) and GIRK4 (Kir3.4). GIRK1-GIRK3 are the predominant subunits in the CNS, with GIRK4 expressed at low levels. Kubo, (1993), Lesage (1994), Kobayashi (1995), Karschin (1996), Kobayashi (1999), Krapivinsky (1995), Kobayashi (1999) Multiple lines of evidence support important roles for GIRK in a variety of physiological processes including the control of heart rate and electrical excitability in a variety of neuronal populations, leading to postulates that GIRK channel modulation as potential target for a variety of therapeutic indications including pain, epilepsy, and reward/addiction. Id. However, a complete lack of selective and effective GIRK activators has prevented further target validation for the many indications where GIRK activation is speculated to be of potential benefit. Id. Indeed, the only compounds that are known to activate GIRK are alcohols (e.g., ethanol) at concentrations of hundreds of millimolar and, recently, the compound naringin has been identified as a GIRK activator; however, the reported EC50 is in excess of 100 µM. Kobayashi (1999), Yow (2011), Aryal (2009)

Figure 6:
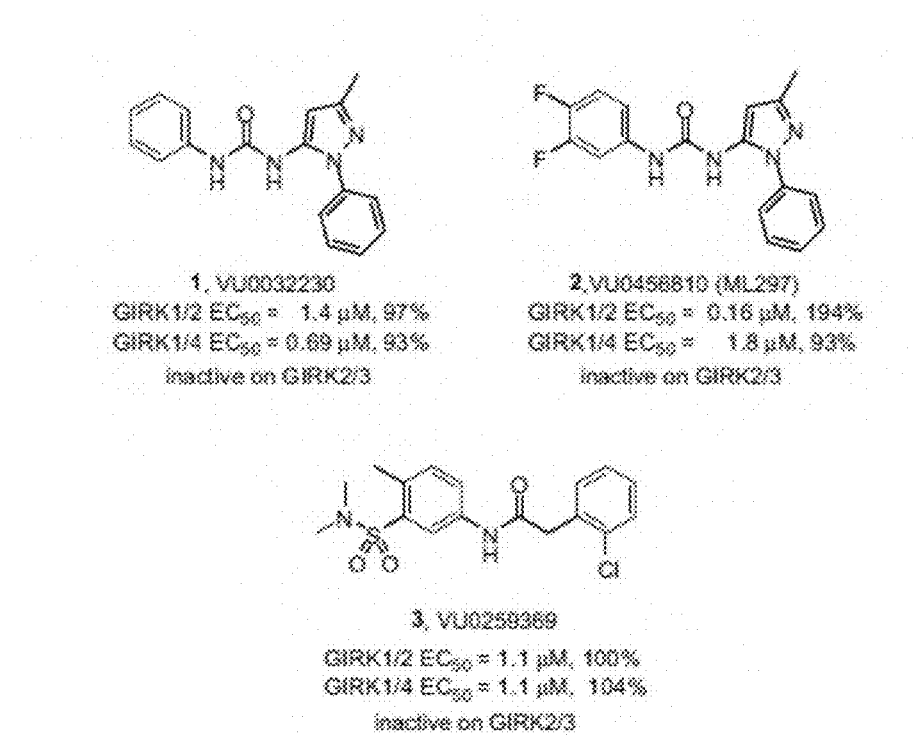
FIG. 6. Structures and GIRK activities of HTS leads 1 and 3, and the optimized.

Based on this limitation in the field, a suite of small molecule GIRK probes were developed. Towards this goal, GIRK activator leads were identified by mining HTS hits obtained from an MLSCN mGlu8 screening project (The MLSCN evolved into the MLPCN in 2008. For more information on the MLPCN and further details on the HTS effort, see: www-.mli.nih.gov/mli/mlpcn), where mGlu8 activity was measured via a thallium flux-based readout of GIRK1/GIRK2. (See Thallium flux assay protocol). Once hits for mGlu8 (mGlu8/Gqi9 calcium flux assay) were triaged, multiple hits remained that were putative GIRK activators with potencies ranging from '1 1M to 10 1M. One series (FIG. 6) from this effort, represented by HTS hit 1 (VU0032230), was subsequently optimized to afford the first selective ('10-fold vs GIRK1/4, inactive on GIRK2/3 and inactive on other K+ channels) GIRK1/2 activator 2 (VU0456810, also known as ML297). Kauffman (2013) Importantly, 2 was centrally penetrant and established anti-epileptic properties in mice via GIRK1/2 activation. The HTS also identified another attractive, and structurally distinct, dual GIRK1/2 and GIRK1/4 activator 3 (VU0259369), and in this example the synthetic strategy and SAR for this lead are detailed.

Figure 7:
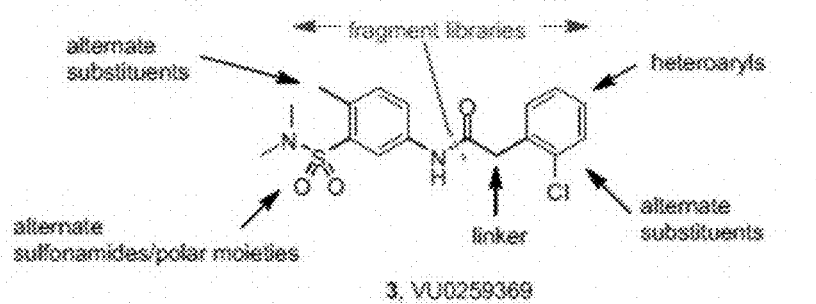
FIG. 7. Chemical optimization plan for 3, consisting of iterative parallel synthesis and fragment libraries.
Figure 8:
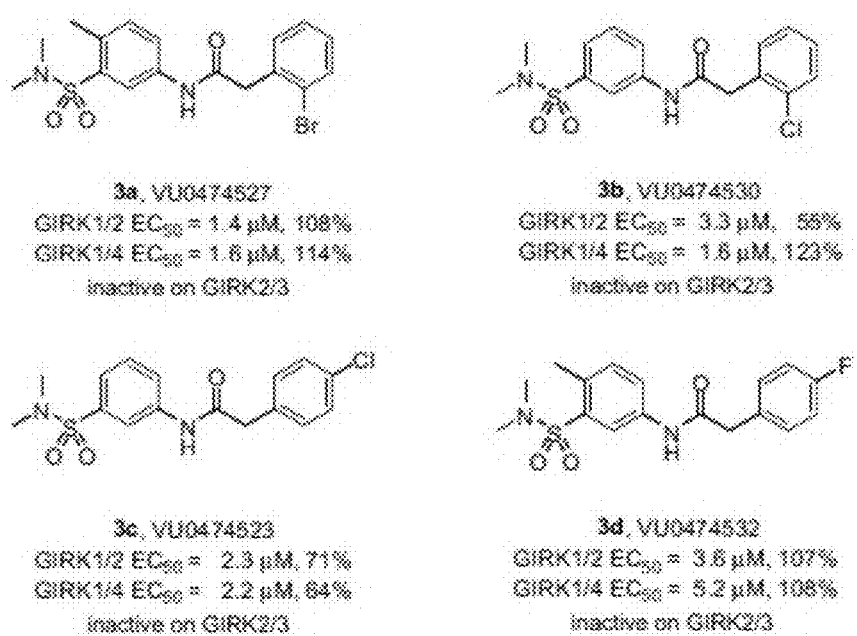
FIG. 8. Representative active GIRK activators from iterative parallel synthesis effort around 3.
Figure 9:
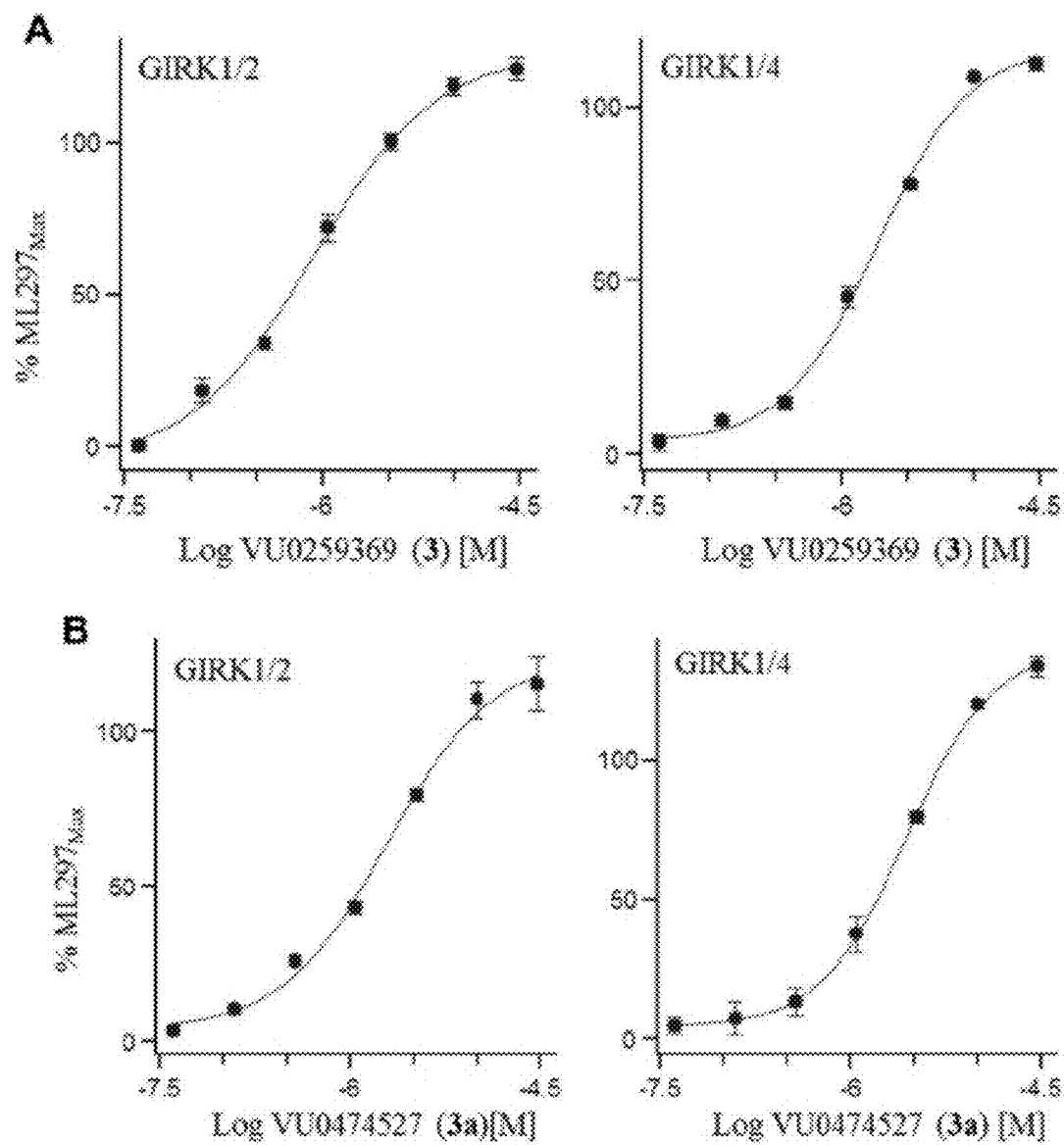

The optimization strategy for 3 is shown in FIG. 7. Here, divergent approaches were pursued in parallel, that consisted of iterative parallel library synthesis and a fragment library approach, to enable both the optimization as well as an attempt to identify a minimum pharmacophore. Kennedy (2008), Lindsley (2004) In short order, over 100 analogs were synthesized (via standard acylation chemistry) and assayed in the GIRK1/2 and GIRK1/4 thallium flux assays, and SAR proved to be shallow for this series, with >50% of the analogs displaying no GIRK activity. The iterative parallel synthesis effort, surveying modifications to the parent 3, afforded few actives (FIG. 8). Of the actives, bromine effectively replaced the chlorine atom, as in 3a, in contrast deletion of the methyl group, providing 3b, maintained potency and efficacy at GIRK1/4, but diminished potency and lost efficacy at GIRK1/2. Moving the halogen of 3 from the 2- to the 4-position, as in 3c and 3d, also led to a diminution in potency at both GIRK1/2 and GIRK1/4. FIG. 9 highlights the GIRK1/2 and GIRK1/4 concentration response curves for 3 and 3a. All attempts to replace or modify the N,N-dimethyl sulfonamide group, incorporation of heterocycles or modification of the linker moiety led to a complete loss of GIRK activity. Fortunately, the fragment libraries proved more productive.

For the fragment libraries (FIG. 7), the 5-(N,N-dimethylsulfonamide)-4-methylphenyl moiety 4 was held constant, and prepared libraries of amide 5 and urea congeners 6 (Scheme 1). In parallel, the 2-(2-chlorophenyl)acetamide portion was held constant, and treated the acid chloride 7 with a variety of anilines to provide analogs 8. Yields for these libraries ranged from 22% to 95% based on the coupling partners employed. (See General Urea Library).

Scheme 1.

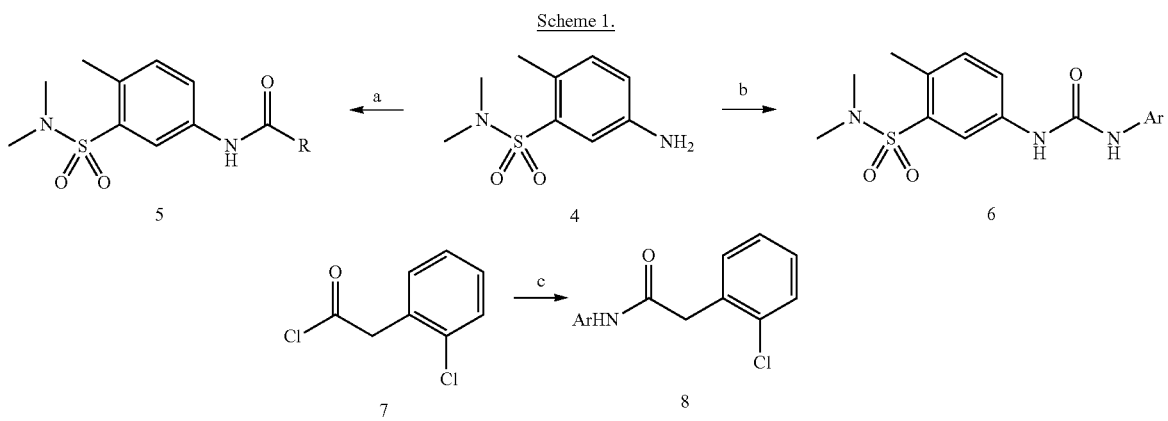

Reagents and conditions:
(a) RCOCl, TEA, DMF, rt, 16 h, 45-95%;
(b) RNCO, DMF, rt, 22-88%;
(c) ArNH2,TEA, DMF, rt, 37-92%.

The amide congeners 5 proved to be uniformly inactive, with the exception of a few C4- to C8-aliphatic amide congeners; however, the GIRK1/2 EC50s were in the 4-10 tM range with modest efficacies (23-91%). In contrast, the urea congeners 6 possessed robust SAR, low micromolar potencies, high efficacy (71-120%) and engendered a slight preference for GIRK1/2 (Table 3). This effort provided dual GIRK1/2 and GIRK1/4 activators such as 6b, 6f and 6j, with a range of full to partial efficacies. This is an important finding, as it is not yet clear if a full or partial GIRK activator will be more ideal in terms of in vivo efficacy, safety and tolerability, and having a range of chemical tools will enable these issues to be addressed. Analogs such as 6h, with a 4-CF3 moiety, proved to be selective for GIRK1/2 (EC50=1.5 tM) over GIRK1/4 (EC50>10 tM), but with low efficacy (26%). Electron rich congeners, such as 6i, were uniformly inactive at both GIRK1/2 and GIRK1/4.

TABLE 3

Structures and GIRK activities of analogs 6

| Compd | Ar | GIRK1/2 $EC_{50}^{a}$ (μM) | GIRK1/2 Efficacy$^{a}$ (%) | GIRK1/4 $EC_{50}^{a}$ (μM) | GIRK1/4 Efficacy$^{a}$ (%) |
|---|---|---|---|---|---|
| 6a | Ph | 1.4 | 94 | 3.9 | 100 |
| 6b | 4-ClPh | 3.3 | 92 | 2.8 | 72 |
| 6c | 3-Cl,4-MePh | 2.9 | 91 | 6.2 | 115 |
| 6d | 4-OMePh | 1.7 | 101 | 5.6 | 104 |
| 6e | 2-FPh | 3.9 | 111 | 7.8 | 72 |
| 6f | 3-FPh | 1.1 | 89 | 1.8 | 55 |
| 6g | 2-ClPh | 2.7 | 94 | 6.8 | 106 |
| 6h | 4-CF$_3$Ph | 15 | 26 | >10 | ND |

TABLE 3-continued

Structures and GIRK activities of analogs 6

| Compd | Ar | GIRK1/2 $EC_{50}^{a}$ (μM) | GIRK1/2 Efficacy$^{a}$ (%) | GIRK1/4 $EC_{50}^{a}$ (μM) | GIRK1/4 Efficacy$^{a}$ (%) |
|---|---|---|---|---|---|
| 6i | 2.5-diOMePh | >10 | ND | >10 | ND |
| 6j | 3-CNPh | 3.9 | 83 | 3.3 | 29 |

$^{a}$Potency values were obtained from triplicate determinations and the reported efficacy values shown are standardized to the efficacy of 2, arbitrarily designated to 100%.
ND = not determined.

Figure 10:
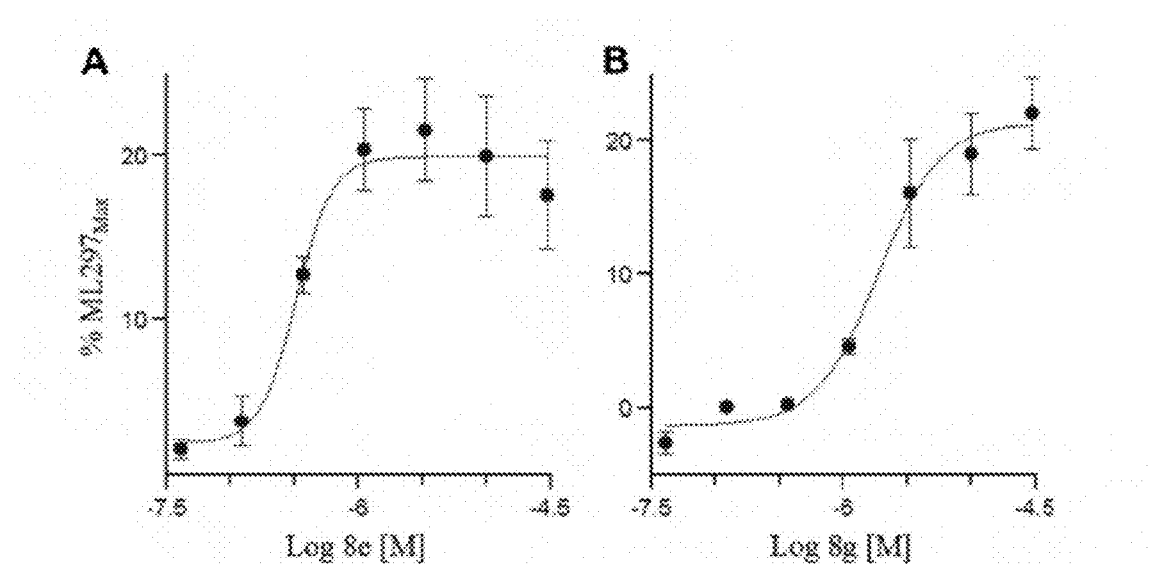
FIG. 10. GIRK activator concentration response curves (CRC) measuring thallium flux. (A) GIRK1/4 (EC50=0.24 LM, 17%) CRC for 8e; (B) GIRK1/4 (EC50=1.8 LM, 22%) CRCs for 8g (See Thallium flux assay protocol).

In analogs 8, where the eastern 2-(2-chlorophenyl)acetamide portion was held constant and diverse anilines were surveyed, interesting SAR emerged (Table 4). SAR was very shallow, and unlike analogs 6, all analogs 8 were devoid of activity at GIRK1/2, affording GIRK1/4 preferring activators. A 4-Cl,3-CF3phenyl amide derivative 8e, was a very potent GIRK1/4 activator (EC50=0.24-tM), but displayed weak, partial activation (17%) of the channel, and was inactive on GIRK1/2. Other electron withdrawing substituents in the 3-position, such as Cl (8g) or CF3 (8h), were selective, partial GIRK1/4 activators; interestingly, electron donating substituents in the 3-position, such as 8i, were inactive at both GIRK1/2 and GIRK1/4. None of the analogs 6 or 8 were active at non-GIRK1 containing GIRK channels, further enabling them as valuable tool compounds to better understand selective GIRK channel activation (see FIG. 10).

TABLE 4

Structures and GIRK activities of analogs 8

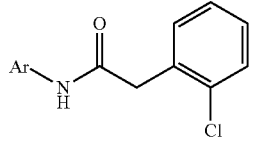

| | | GIRK1/2 | | GIRK1/4 | |
|---|---|---|---|---|---|
| Compd | Ar | $EC_{50}^a$ (µM) | Efficacy$^a$ (%) | $EC_{50}^a$ (µM) | Efficacy$^a$ (%) |
| 8a | 4-F,3-SO$_2$MePh | >10 | ND | >10 | ND |
| 8b | 3-t-BuPh | 5.9 | 44 | 2.7 | 76 |
| 8c | 3-OCHF$_2$Ph | >10 | ND | 7.8 | 119 |
| 8d | 3-Cl,5-CF$_2$Ph | >10 | ND | >10 | ND |
| 8e | 4-Cl,3-CF$_3$Ft | >10 | ND | 0.24 | 17 |
| 8f | 4-ClPh | >10 | ND | >10 | ND |
| 8g | 3-ClPh | >10 | ND | 1.8 | 22 |
| 8h | 4-CF$_2$Ph | >10 | ND | 2.1 | 20 |
| 8i | 3-MePh | >10 | ND | >10 | ND |

$^a$Potency values were obtained from triplicate determinations and the reported efficacy values shown are standardized to the efficacy of 2, arbitrarily designated to 100%.
ND = not determined.

In summary, described in this Example are the synthesis and one of the first accounts of SAR for a novel series of rarely described GIRK activators, indicating that GIRK activators can be identified from HTS campaigns and optimized. SAR proved shallow, and an iterative parallel synthesis approach provided little improvement in terms of potency or efficacy at GIRK1/2 or GIRK1/4. Instead a fragment library approach afforded a diverse array of GIRK activators that included dual GIRK1/2 and GIRK1/4 activators, GIRK1/2 preferring activators and GIRK1/4 selective activators possessing a wide range of efficacy (from weak partial to full activation), and devoid of activity at non-GIRK 1-containing GIRK channels. Additional characterization and refinements are in progress and will be reported in due course.

Thallium Flux Assay Protocol:

Compounds were dissolved in DMSO, transferred to 384-well polypropylene plates, and serially diluted in DMSO using and Agilent Bravo (11-points, threefold dilutions). Serially diluted plates were dispensed to daughter plates using a Labcyte Echo555 and diluted to twofold over their target assay concentration with 20 mM HEPES-buffered (pH 7.4) Hanks Balanced Salt Solution (HBSS), hereafter referred to as Assay Buffer, using a Thermo Fisher Combi. Twenty-thousand HEK-293 cells/well stably transfected with the ion channel subunits of interest (e.g., GIRK1/GIRK2, GIRK1/GIRK4) were plated into 384-well, black-walled, clear-bottom, amine-coated coated plates in 20 LL/well alpha-minimal essential medium (MEM) supplemented with 10% (v/v) fetal bovine serum and incubated overnight in a 5% $CO_2$ incubator at 37° C. Cell culture medium was removed from cell plates and replaced with 20 LL/well Assay Buffer. Twenty microliters/well of 0.5 LM of the thallium-sensitive dye, Thallos-AM (TEFlabs, Austin Tex.) in Assay Buffer was added to cell plates. Cell plates were incubated for 60 min at room temperature and then dye-loading solution was removed from cell plates and replaced with 20 LL/well Assay Buffer. Dye loaded and washed cell plates were transferred to a Hamamatsu FDSS 6000 and a double-addition protocol was initiated. After 10s, 20 LL/well of 20 LM test compound in 0.2% DMSO and Assay Buffer was added. After 4 min 10 LL/well of a 5× sodium bicarbonate-based thallium stimulus buffer (20 mM HEPES pH 7.4, 135 mM NaHCO3, 2 mM CaSO4, 1 mM MgSO4, 5 mM glucose, 12 mM Tl2SO4) was added and 2 more minutes of data collection followed. Fluorescence data were collected at 1 Hz. Data analysis: Waveform signals (fluorescence intensity vs time normalized by dividing each fluorescence value (F) by the initial fluorescence value for each trace (F0)) were reduced to single values by subtracting the average normalized waveform from vehicle control wells from each wave on the plate followed by obtaining the slope of the change in fluorescence immediately after the addition of the thallium stimulus. Slope values were normalized as a percentage of the slope obtained by the addition of a maximally effective concentration of the GIRK activator, ML297 (e.g., an efficacy value of 100% means that the compound's maximum apparent efficacy equals that of ML297). Curve fits for normalized slope values were obtained using a four-parameter logistic equation in the Excel add-in, XLfit.

General Urea Library:

To a solution of 5-amino-N,N,2-trimethylbenzenesulfonamide (4) (15 mg, 0.07 mmol, 1.0 equiv) in DMF (1.0 mL) was added an isocyanate (0.07 mmol, 1.0 equiv) at rt. After 12 h, the reaction was purified by reverse phase HPLC to afford the desired urea. General Amide Library: To a solution of 5-amino-N,N,2-trimethylbenzenesulfonamide (4) (15 mg, 0.07 mmol, 1.0 equiv) in DMF and TEA (4:1, 1.0 mL) was added the acid chloride (0.084 mmol, 1.1 equiv) at rt. Once the reaction was complete by LCMS, the reaction was filtered and purified by reverse phase HPLC to afford the desired amide. General urea library: To a solution of 5-amino-N,N,2-trimethylbenzenesulfonamide (4) (15 mg, 0.07 mmol, 1.0 equiv) in DMF and TEA (4:1, 1.0 mL) was added the acid chloride (0.084 mmol, 1.1 equiv) at rt. Once the reaction was complete by LCMS, the reaction was filtered and purified by reverse phase HPLC to afford the desired amide.

Example 3

Figure 11:
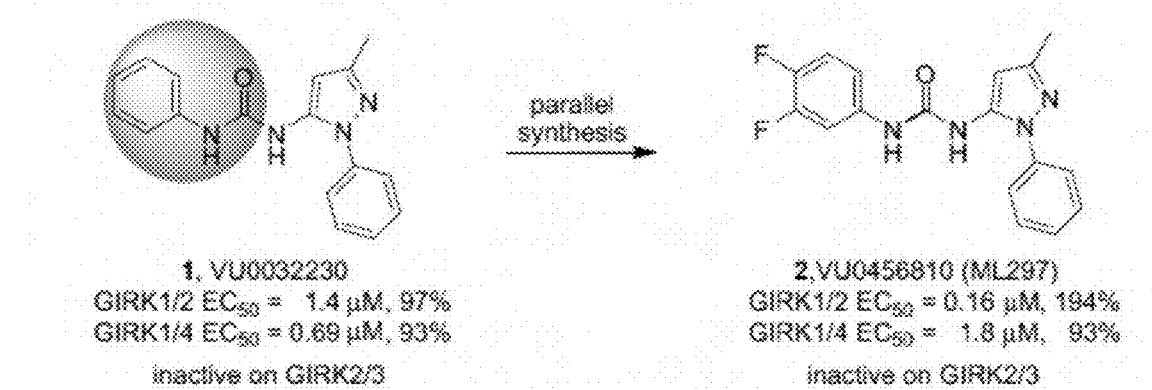
FIG. 11. Structures and GIRK activities of HTS GIRK activator lead 1 and the optimized GIRK1/2 and GIRK1/4 activator 2 (ML297).

The $K_{i,}3.1$-3.4 family of inward-rectifying potassium channels, also referred to as G protein regulated Inwardly Rectifying Potassium ($K^+$) or GIRK1-4 channels, modulate cell excitability, and have been implicated in a number of crucial physiological processes.*Kubo* (1993); *Lesage* (1994); *Kobayashi* (1995); *Karschin* (1996); *Luscher* (2010); *Krapivinsky* (1995); *Kobayashi* (1999) Due a lack of potent and selective small molecule GIRK activators (the only known activators are alcohols (e.g., ethanol) and naringin with $_{EC50s}$>100 lM) and inhibitors (only the weak and unselective SCH23390 IC50s '4-8 lM), target validation for GIRK activation and inhibition in multiple therapeutic areas has been hindered.*Kubo* (1993); *Lesage* (1994); *Kobayashi* (1995); *Karschin* (1996); *Luscher* (2010); *Krapivinsky* (1995); *Kobayashi* (1999); *Yow* (2011); *Aryal* (2009) With this in mind, GIRK activator 1 (VU0032230) was identified from an MLSCN HTS campaign that employed a thallium-flux based readout of GIRK1/GIRK2. *Kauffmann* (2013) (Note that the MLSCN evolved into the MLPCN in 2008. For more information on the MLPCN and further details on the HTS effort, see: www-.mli.nih.gov/mli/mlpcn.). Subsequent chemical optimization, via parallel synthesis (FIG. 11), evaluated alternate ureas and linkage moieties, that ultimately afforded the first selective ('10-fold versus GIRK1/4, inactive on GIRK2, GIRK2/3 and on the $K^+$ channels tested) GIRK1/2 activator 2 (VU0456810, also known as ML297).*Kauffmann* (2013) ML297 was shown to possess a favorable DMPK profile, was centrally penetrant and established proof of concept for GIRK1/2 activation in preclinical epilepsy models.*Kauffmann* (2013) Described in this example are further multi-dimensional SAR exploration of 2 that resulted in the identification of additional GIRK activators, and 'molecular switches'*Sharma* (2008); *Wood* (2011); *Cheung* (2012) that afforded the selective GIRK inhibitors.

Figure 12:
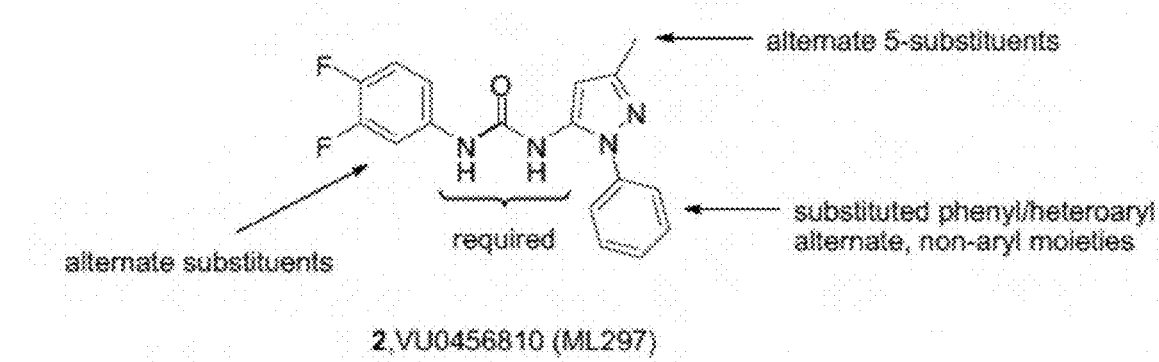
FIG. 12. Chemical optimization plan for 2, employing parallel synthesis.

FIG. 12 highlights the chemical optimization plan for 2 to survey multiple dimensions of the molecule. In the previous work that afforded 2, SAR was limited to alternate ureas and alternate linkages for the urea moiety; moreover, the urea linkage was found to be required, and not even N-Me congeners of either NH possessed any GIRK activity. Interestingly, all of the analogs assayed were either GIRK activators or inactive.

For the first library, the 3-methyl pyrazole and the 3,4-difluorophenyl moieties of 2 were held constant, and surveyed a variety of alternatives for the N-Ph group. In this instance, all of the N-functionalized-5-amino-3-methylpyrazoles 3 were commercially available, and simply reacted with 3,4-difluorophenyl isocyanate 4 to deliver analogs 5 (Scheme 2). This library afforded a number of GIRK activators, including the benzyl congener 5d, the most potent dual GIRK1/2 (EC50=0.07 tM, 87%) and GIRK1/4 (EC50=0.11 tM, 99%) activator identified to date. All attempts to incorporate a basic amine, represented by pyridyl analogs 5c and 5e, resulted in a substantial loss of GIRK activity. While comparable to the parent 2, both the 4-fluorophenyl congener 5b and the chemically distinct trifluoroethyl analog 5a, were substitutions worthy of further analogs. Additional analogs of 5d, surveying alternate ureas, led to a family of dual GIRK1/2 and GIRK1/4 activators. Importantly, all analogs 5 were inactive on non-GIRK1 containing channels (Table 5).

TABLE 5

Structures and GIRK activities of analogs 5

|  |  | GIRK1/2 | | GIRK1/4 | |
|---|---|---|---|---|---|
| Compd | R | EC$_{50}$ (µM)$^a$ | Efficacy$^b$ (%) | EC$_{50}$ (µM)$^a$ | Efficacy$^b$ (%) |
| 5a | -CH$_2$CF$_3$ | 0.46 | 96 | 1.3 | 103 |
| 5b | 4-F-phenyl | 0.19 | 78 | 0.54 | 57 |
| 5c | 2-pyridyl | >10 | 78 | >30 | ND |
| 5d | benzyl | 0.07 | 87 | 0.11 | 99 |
| 5e | 4-pyridyl | >10 | 88 | >30 | ND |

ND = not determined.
$^a$Potency values were obtained from triplicate determinations.
$^b$Reported efficacy values shown are standardized to the efficacy of 2, arbitrarily designated to 100%.

Scheme 2. Synthesis of analogs 5.

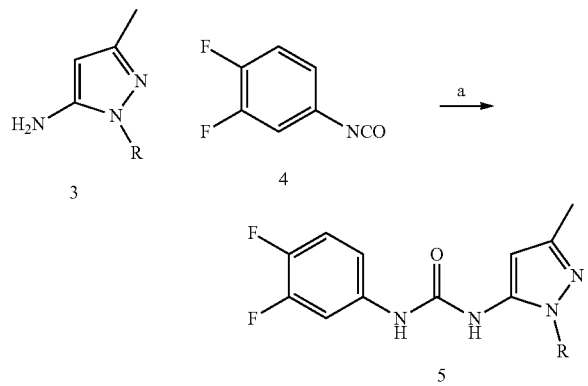

Reagents and conditions.
(a) CH$_2$Cl$_2$, rt, 16 h, 73-98%.

In parallel, a library of analogs 6 was constructed that held the 3,4-difluorophenyl and the N-phenyl moieties constant, and evaluated alternative substituents in the 3-position of the pyrazole, following a slight perturbation of Scheme 2. This effort generated unique, textured SAR and, for the first time for GIRK, the identification of 'molecular switches',[Sharma (2008); Wood (2011); Cheung (2012)] that modulated the mode of pharmacology from activator to inhibitor (Table 6). As with the activators, where efficacy is normalized to 2, the only known GIRK inhibitor SCH23390 (a D1 antagonist with off-target GIRK activity) was employed,[Terry (1994)] and percent inhibition with SCH23390 was normalized affording 100% inhibition.

TABLE 6
Structures and GIRK activities of analogs 6

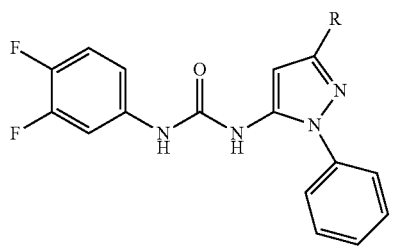

| Compd | R | GIRK1/2 EC$_{50}$ (μM)$^a$ IC$_{50}$ (μM)$^a$ | GIRK1/2 Effic.$^b$ (%) IC$_{50}$ (μM)$^a$ | CAT ACT INH | GIRK1/4 EC$_{50}$ (μM)$^a$ IC$_{50}$ (μM)$^a$ | GIRK1/4 Effic.$^b$ (%) Effic.$^b$ (%) | CAT ACT INH |
|---|---|---|---|---|---|---|---|
| 6a | phenyl | >30 30 | ND ND | ACT INH | 30 30 | ND ND | ACT INH |
| 6b | cyclopropyl | 0.41 NA | 32 NA | ACT INH | 30 NA | ND NA | ACT INH |
| 6c | isopropyl | NA 2.0 | NA 136 | ACT INH | NA 1.4 | NA 150 | ACT INH |
| 6d | cyclobutyl | 30 30 | ND ND | ACT INH | 30 30 | ND ND | ACT INH |
| 6e | cyclopentyl | NA 5.1 | NA 85 | ACT INH | NA 4.1 | NA 88 | ACT INH |
| 6f | CF$_3$ | 30 30 | ND ND | ACT INH | 30 30 | ND ND | ACT INH |

TABLE 6-continued

Structures and GIRK activities of analogs 6

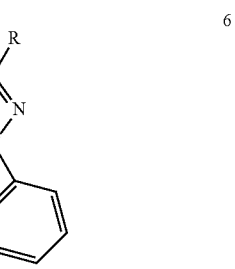

6

| Compd | R | GIRK1/2 | | CAT | GIRK1/4 | | CAT |
|---|---|---|---|---|---|---|---|
| | | $EC_{50}$ (μM)[a] $IC_{50}$ (μM)[a] | Effic.[b] (%) $IC_{50}$ (μM)[a] | ACT INH | $EC_{50}$ (μM)[a] $IC_{50}$ (μM)[a] | Effic.[b] (%) Effic.[b] (%) | ACT INH |
| 6g | 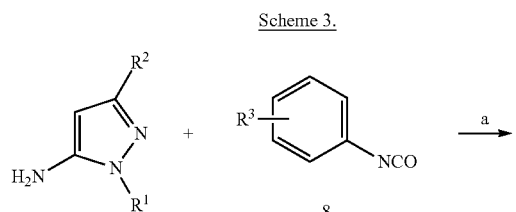 | NA 0.65 | NA 95 | ACT INH | NA 0.56 | NA 67 | ACT INH |

ND = not determined; ACT = activator: INH = inhibitor: NA = not applicable.
aPotency values were obtained from triplicate determinations.
bReported efficacy values are standardized to the efficacy of 2, arbitrarily designated to 100% for activators, and standardized to SCH3320, arbitrarily designated to full inhibition (100%), for inhibitors.

Here, replacement of the 3-methyl group with either a phenyl (6a), CF3 (6f) or cyclobutyl moiety (6d), led to a complete loss of GIRK activity. A cyclopropyl group (6b) proved to be a selective, GIRK1/2 partial activator (EC50=0.41 tiM, 32%); in contrast, an isopropyl derivative (6c) was a dual GIRK1/2 (IC50=2.5 tiM, 136%) and GIRK1/4 (IC50=4.1 tiM, 88%) inhibitor, and represented the first example of a GIRK 'molecular switch'[Sharma (2008); Wood (2011); Cheung (2012)] While this phenomenon is common amongst Family A and C allosteric GPCR ligands[Sharma (2008); Wood (2011)] and, more recently, KCNQ2 ion channel ligands[Cheung (2012)] and Ca channel modulators,[O'neil (1988)] it has not yet been reported for GIRK ligands. Ring expansion from the inactive cyclobutyl (6d) to a cyclo-pentyl analog (6e) restores GIRK activity, but as a weak dual GIRK 1/2 and GIRK1/4 inhibitor. Quite unexpectedly, a cyclopropyl methyl congener (6g) was a potent, and fully efficacious GIRK1/2 (IC50=0.65 tiM, 95%) and GIRK1/4 (IC50=0.56 tiM, 67%) inhibitor, whereas 6b, the cyclopropyl analog was a selective GIRK1/2 activator. Importantly, all analogs 6 were inactive on nonGIRK containing GIRK channels. Based on the SAR data generated from these two libraries, it was time to explore additional isocyanates within 6 and to merge productive modifications noted in analogs 5 and 6, and assess if these would either be additive or if additional 'molecular switches'[Sharma (2008); Wood (2011); Cheung (2012)] be discovered (Scheme 3).

Scheme 3.

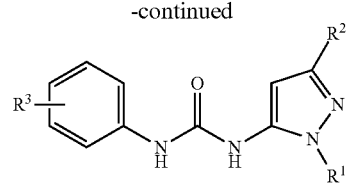

-continued

Synthesis of analogs 9.
Reagents and conditions.
(a) CH₂Cl₂, rt, 16 h, 64-95%.

Figure 13:
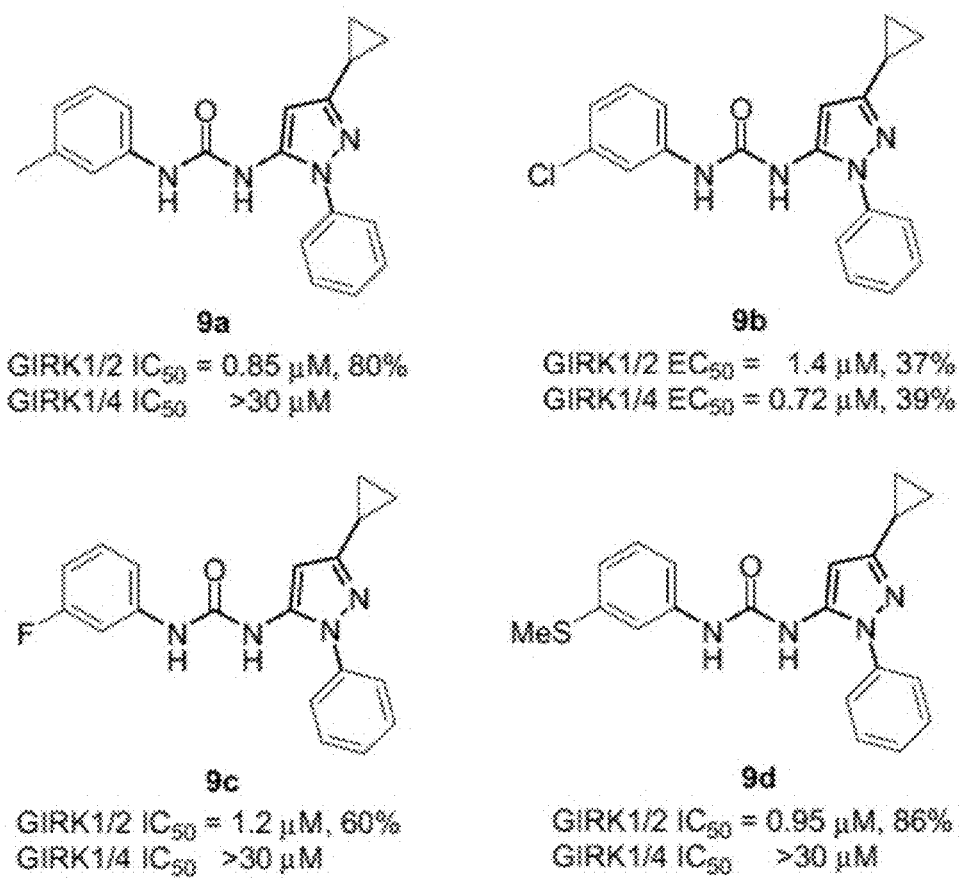
FIG. 13. Selected analogs 9 where nature of phenyl substituent converts a 3-cyclopropyl GIRK1/2 activator scaffold into GIRK1/2 selective inhibitors.

First, the N-phenyl and N-benzyl moieties in analogs 5 were employed, with the cyclopropyl, isopropyl and cyclopropyl methyl groups found in active analogs 6, and explored a diverse array of isocyanates to deliver 120 analogs 9 from a matrix library (2×3×20). These new analogs displayed a wide range of GIRK1/2 and GIRK1/4 selectivity profiles, as well as promiscuous modulation in the mode of pharmacology from activator to inhibitor. Whereas the cyclopropyl group in 6b afforded a selective GIRK1/2 partial activator, other substitutions on the phenyl ring of the urea afforded both weak activators (EC50s 0.9-5 lM, 13-65%) and potent, GIRK1/2 selective inhibitors. FIG. 13 highlights some representative 3-cyclopropyl, N-phenyl analogs 9a-d, where the nature of the 3-substitutent modulates the mode of pharmacology.

Figure 14:
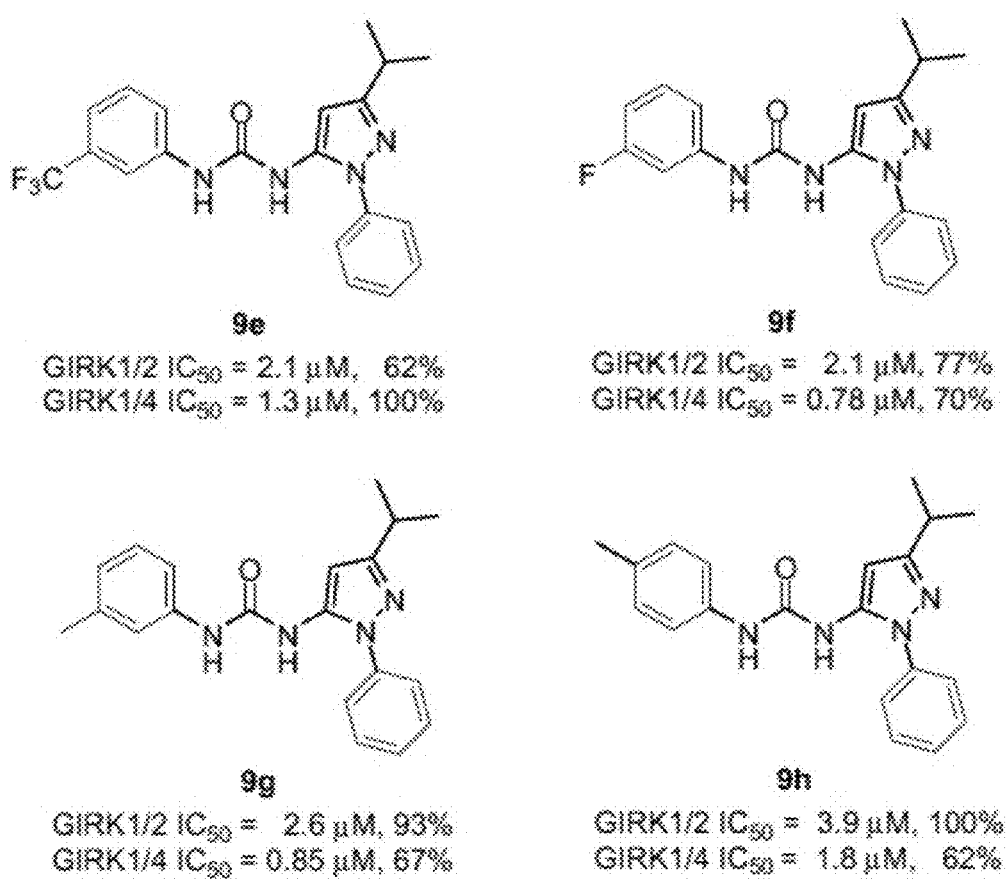
FIG. 14. Selected analogs 9 where the 3-isopropyl moiety engenders exclusive GIRK inhibition, often slightly favoring GIRK1/4.

In sharp contrast, additional analogs of the isopropyl derivative 6c were exclusively either GIRK inhibitors, or inactive, and many displayed a slight preference for GIRK1/4 over GIRK1/2 (FIG. 14). Interestingly, the optimal phenyl substituents in the expanded 6b library (analogs 9a-d), were not optimal for the 6c scaffold (9e-h), yet substituents in the 3-position were uniformly more active.

Figure 15:
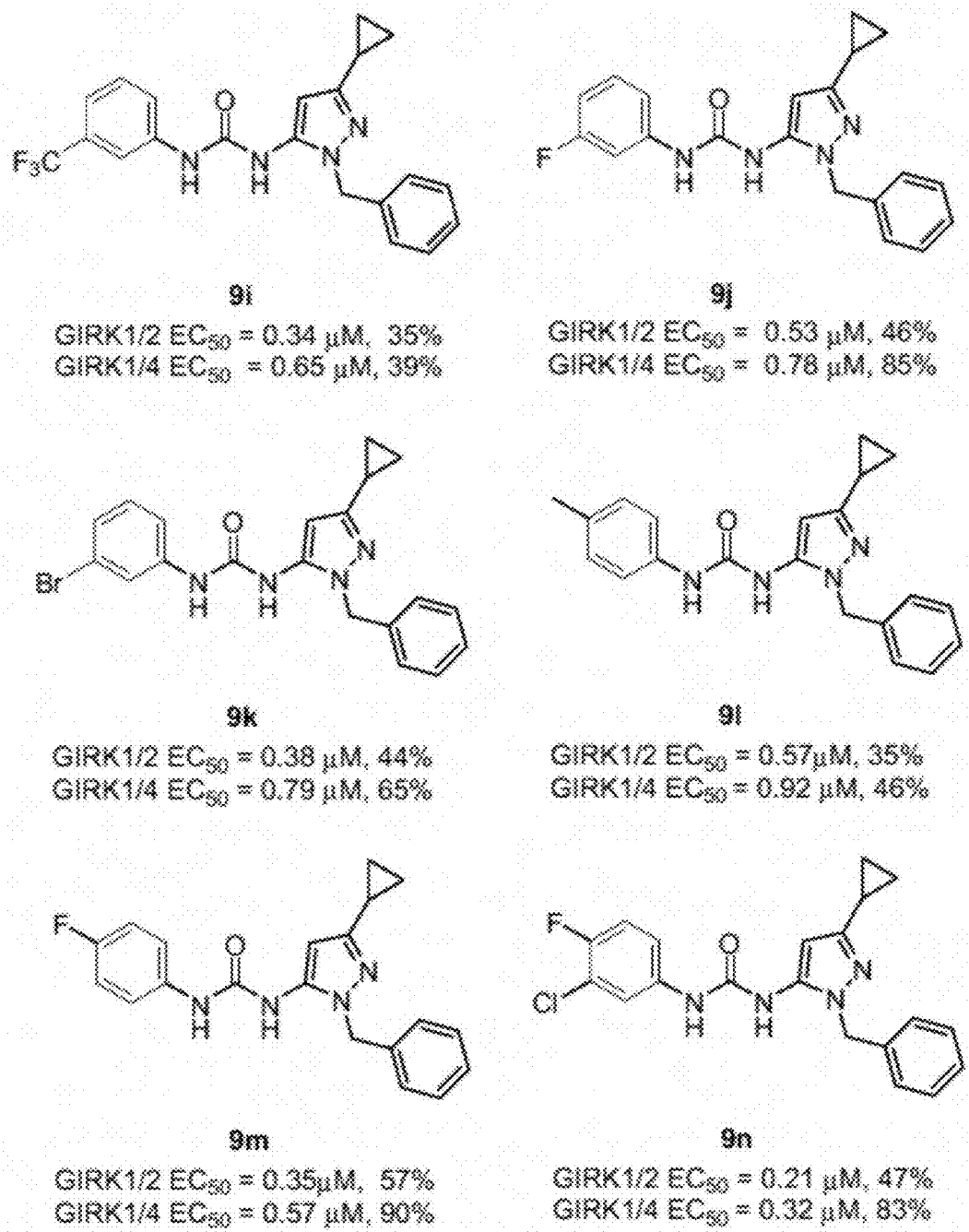
FIG. 15. Selected analogs 9 where a 3-cyclopropyl, N-benzyl GIRK1/2 activator scaffold uniformly affords potent, dual GIRK1/2 and GIRK1/4 activators with variable efficacies.

A library combining the 3-cyclopropyl moiety with the N-ben-zyl group, functionalities that both imparted GIRK activation, provided highly potent and efficacious dual GIRK1/2 and GIRK1/4 activators (FIG. 15). The SAR within this series was shallow, with virtually all substituents on the aryl ring affording submicromolar, dual GIRK1/2 and GIRK1/4 activators.

Figure 16:
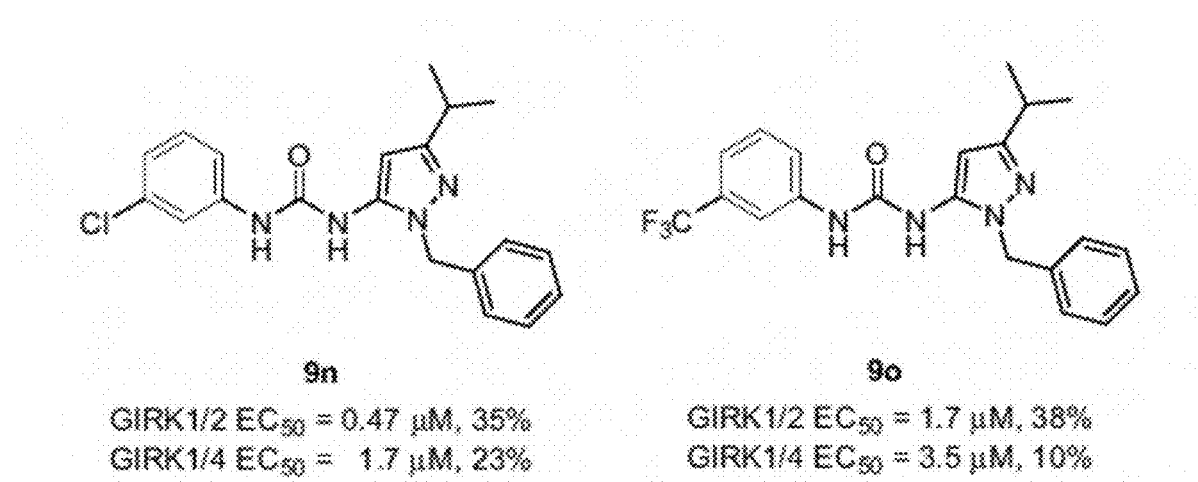
FIG. 16. Selected analogs 9 with 3-isopropyl, N-benzyl motif affords low efficacy GIRK1/2 and dual GIRK1/2 and GIRK1/4 activators.

The corresponding 3-isopropyl, N-benzyl congener library afforded fewer active compounds, and with the exception of a few low efficacy (<10%) GIRK1/2 preferring activators, the majority of these analogs were either GIRK1/2 selective or dual GIRK1/2 and GIRK1/4 inhibitors (FIG. 16).

Figure 17:
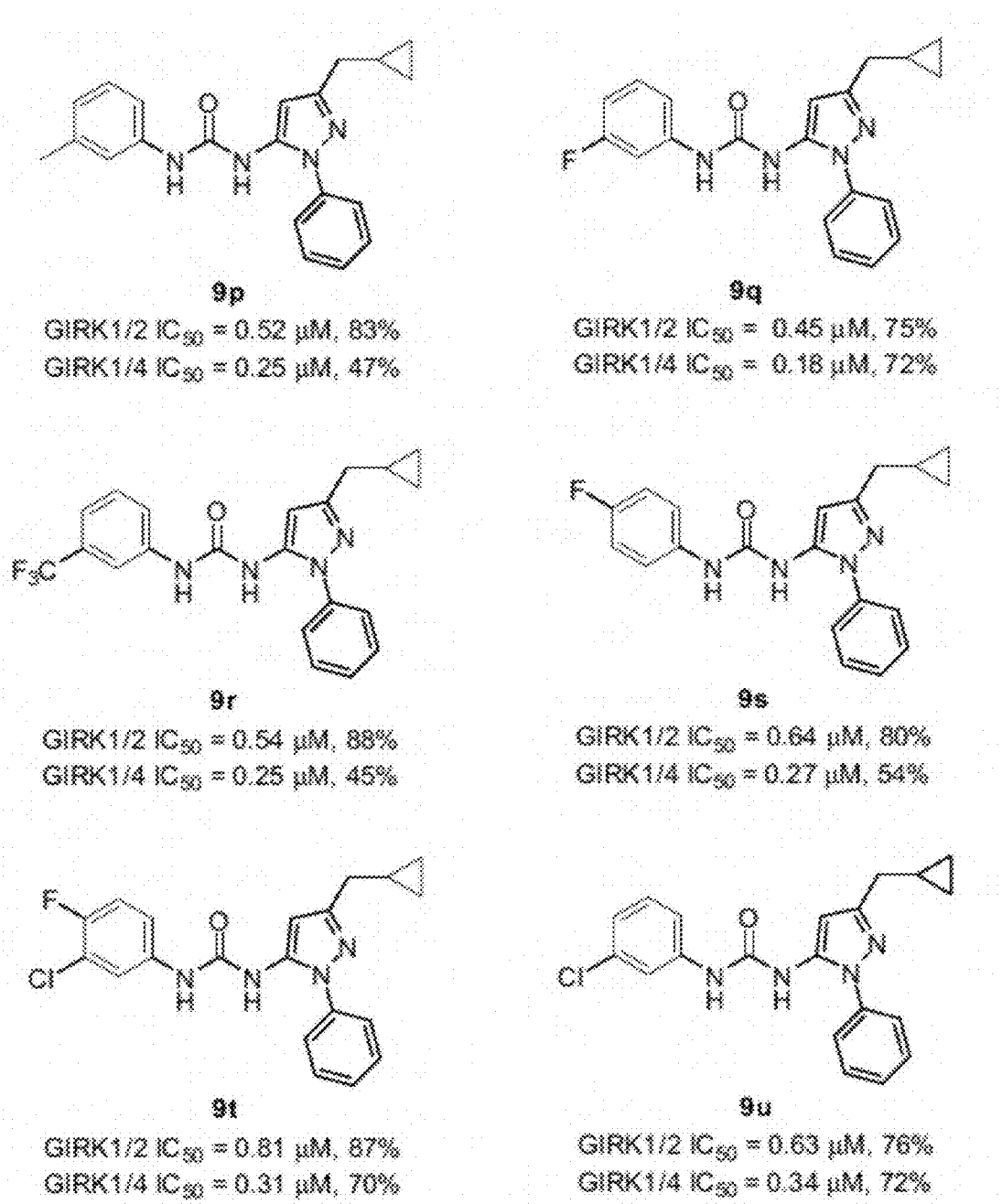
FIG. 17. Selected analogs 9 with 3-cyclopropyl, N-phenyl motif afford highly potent dual GIRK1/2 and GIRK1/4 inhibitors.

The cyclopropylmethyl derivative 6g was a dual GIRK1/2 and GIRK1/4 inhibitor, and replacement of the N-phenyl with an N-benzyl group provided only weak to inactive analogs. However, further evaluation of alternate ureas within the N-phenyl 6g series provided a number of sub-micromolar dual GIRK1/2 and GIRK1/4 inhibitors (FIG. 17). Here, SAR lacked texture, with virtually any substituents on the urea phenyl ring providing GIRK inhibitors of comparable potency.

Figure 18:
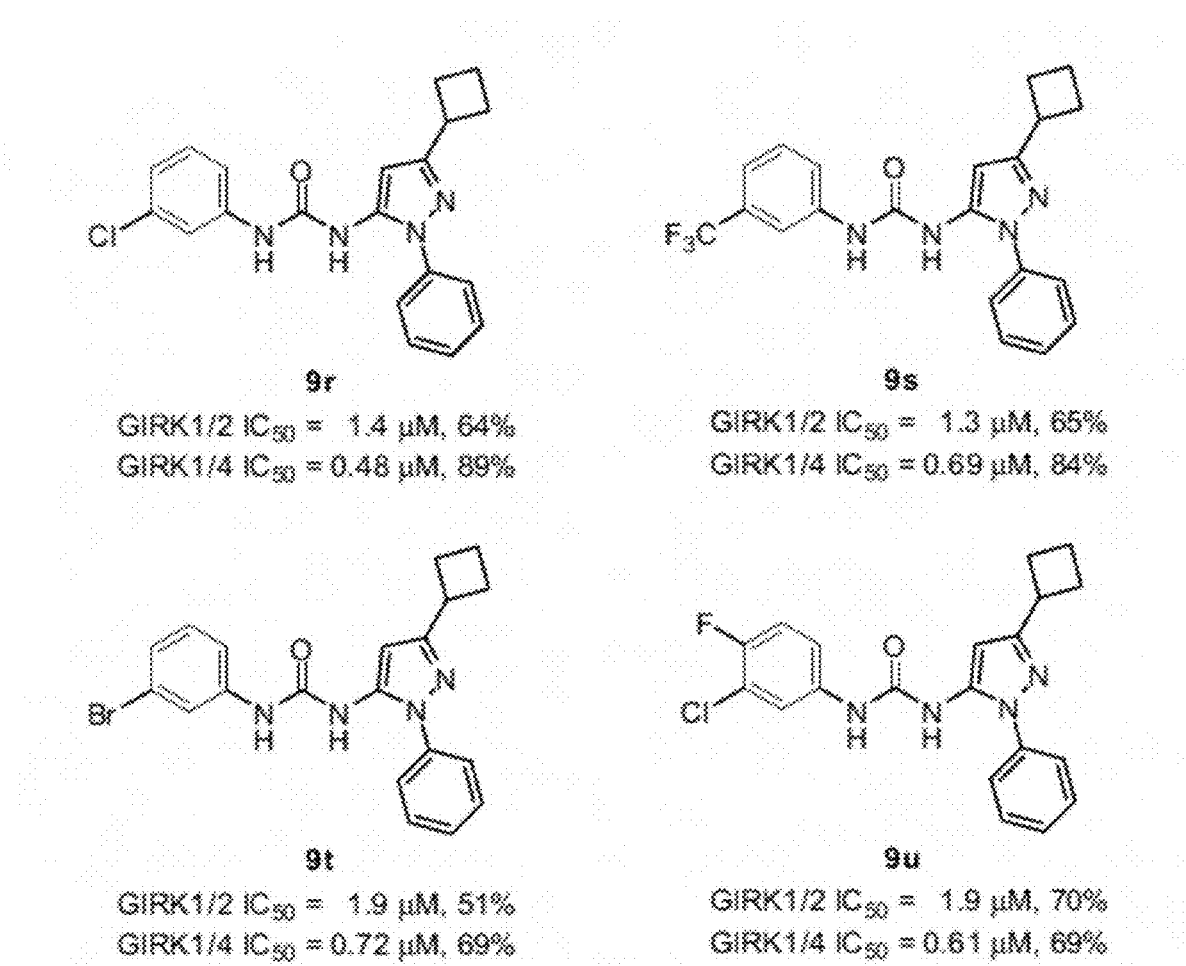
FIG. 18. Selected analogs 9 with 3-cyclobutyl, N-phenyl motif afford GIRK1/4 preferring inhibitors.

Finally, these library efforts highlighted the impact of slight structural variations leading to dramatic changes in GIRK channel selectivity, mode of GIRK pharmacology, and in some cases, an order of magnitude gain or loss of GIRK activity. Therefore, an expanded library was prepared around the 3-cylobutyl analog 6d to determine if GIRK activity could be achieved with alternate functionality. While >90% of these analogs were inactive, several emerged that displayed activity as GIRK inhibitors, with a slight preference for GIRK1/4 (FIG. 18). As seen earlier, substituents in the 3-position are preferred, and groups in the 4-position generally abolish GIRK1/4 inhibition.

In general, these analogs possess high c log Ps (>4), but experimental log P values range from 3.2 to 3.9. The majority of GIRK ligands reported herein display moderate protein binding in rat (1-3% free) and human (1-4% free), moderate intrinsic clearance (CLINT<40 mL/min/kg) and very clean CYP profiles (>20 lM versus 3A4, 2D6, 2C9 and 1A2). Studies probing in vivo PK and CNS exposure are in progress.

In summary, a multi-dimensional SAR campaign was detailed based on a potent, efficacious and selective GIRK1/2 activator (10-fold versus GIRK1/4 and inactive on GIRK2/3) ML297. Further chemical optimization through an iterative parallel synthesis effort identified multiple 'molecular switches' that modulated the mode of pharmacology from activator to inhibitor, as well as engendering varying selectivity profiles for GIRK1/2 and GIRK1/4. Importantly, these compounds were all inactive on nonGIRK1 containing GIRK channels. However, SAR was challenging as subtle structural modifications had large effects on both mode of pharmacology and GIRK1/2 and GIRK1/4 channel selectivity. Despite the optimization challenges, this effort afforded potent and selective GIRK inhibitors, activators with improved potency/efficacy, and a valuable set of tool compounds to further dissect the roles of GIRK channels in various pathological states. Detailed molecular pharmacology studies are underway (e.g., developing mutants that exchange various domains between GIRK1/2 with GIRK 2/3) to understand the mode/site of binding of these novel GIRK ligands and attempt to elucidate the origins of the 'molecular switches'. Further efforts and refinements are in progress and will be reported in due course.

Throughout this document, various references are mentioned. All such references are incorporated herein by reference, including the references set forth in the following list:

REFERENCES

1. Logothetis, D. E., Kurachi, Y., Galper, J., Neer, E. J. & Clapham, D. E. The βγ subunits of GTP-binding proteins activate the muscarinic $K^+$ channel in heart. *Nature* 325, 321-326 (1987). Kubo Y, Reuveny E, Slesinger P A, Jan Y N, Jan L Y. (1993) Primary structure and functional expression of a rat G-protein-coupled muscarinic potassium channel. Nature. 364(6440):802-6.
2. Wickman, K. D. et al. Recombinant G-protein βγ-subunits activate the muscarinic-gated atrial potassium channel. *Nature* 368, 255-257 (1994).
3. Reuveny E. et al. Activation of the cloned muscarinic potassium channel by G protein βγ subunits. *Nature* 370, 143-146 (1994).
4. Lesage F et al. (1994) Cloning provides evidence for a family of inward rectifier and G-protein coupled K+ channels in the brain. FEBS Lett. 353(1):37-42.
5. Krapivinsky G et al. (1995) The G-protein-gated atrial K+ channel IKACh is a heteromultimer of two inwardly rectifying K(+)-channel proteins. Nature. 374(6518):135-41.
6. Luscher C & Slesinger P (2010) Emerging roles for G protein-gated inwardly rectifying potassium (GIRK) channels in health and disease. Nat Rev Neurosci. 11:301-315.
7. Kloukina V, Herzer S, Karlsson N, Perez M, Daraio T, Meister B. (2012) G-protein-gated inwardly rectifying K+ channel 4 (GIRK4) immunoreactivity in chemically defined neurons of the hypothalamic arcuate nucleus that control body weight. J Chem Neuroanat. 44(1):14-23.
8. Hedin K E, Lim N F & Clapham D E. (1996) Cloning of a *Xenopus laevis* inwardly rectifying K+_channel_subunit that permits GIRK1 expression of IKACh currents in oocytes. Neuron 16(2):423-9.
9. Inanobe, A. et al. (1999) Characterization of G-protein-gated $K^+$ channels composed of Kir3.2 subunits in dopaminergic neurons of the substantia nigra. *J. Neurosci.* 19, 1006-1017.
10. Cruz, H. G. et al. Bi-directional effects of $GABA_B$ receptor agonists on the mesolimbic dopamine system. *Nature Neurosci.* 7, 153-159 (2004).
11. Fernández-Alacid L, et al. (2009) Subcellular compartment-specific molecular diversity of pre- and post-synaptic GABA-activated GIRK channels in Purkinje cells. J Neurochem. 110(4):1363-76.
12. Lujan R, Maylie J & Adelman J. (2009) New sites of action for GIRK and SK channels. Nat Rev Neurosci. 10:475-480.
13. Yamada K et al. (2012) Association study of the KCNJ3 gene as a susceptibility candidate for schizophrenia in the Chinese population. Hum Genet. 131(3):443-51.
14. Nishizawa D et al. (2009) Association between KCNJ6 (GIRK2) gene polymorphisms and postoperative analgesic requirements after major abdominal surgery. PLoS One. 4(9):e7060.
15. Smith S B et al. (2008) Quantitative trait locus and computational mapping identifies Kcnj9 (GIRK3) as a candidate gene affecting analgesia from multiple drug classes. Pharmacogenet Genomics. 18(3):231-41.
16. Kang S J, et al. (2012) Family-based genome-wide association study of frontal theta oscillations identifies potassium channel gene KCNJ6. Genes Brain Behav. 712-9.
17. Jabbari J, Olesen M S, Holst A G, Nielsen J B, Haunso S & Svendsen J H. (2011) Common polymorphisms in KCNJ5 are associated with early-onset lone atrial fibrillation in Caucasians. Cardiology. 118(2):116-20.
18. Zennaro M C & Jeunemaitre X. (2011) Mutations in KCNJ5 gene cause hyperaldosteronism. Circ Res. 108(12):1417-8.

19. Bhave G, Lonergan D, Chauder B A & Denton J S. (2010) Small-molecule modulators of inward rectifier K+ channels: recent advances and future possibilities. Future Med Chem. 2(5):757-74.
20. Machida T et al. (2011) Effects of a highly selective acetylcholine-activated K+ channel blocker on experimental atrial fibrillation. Circ Arrhythm Electrophysiol. 4(1): 94-102.
21. Kobayashi T et al. (1999) Ethanol opens G-protein-activated inwardly rectifying K+ channels. Nat Neurosci. 2(12):1091-7.
22. Aryal P, Dvir H, Choe S & Slesinger P A. (2009) A discrete alcohol pocket involved in GIRK channel activation. Nat Neurosci. 12(8):988-95.
Yow T T et al. (2011) Naringin_directly activates inwardly rectifying potassium channels at an overlapping binding site to tertiapin-Q. Br J Pharmacol.163(5): 1017-33.
23. Nishizawa D, Gajya N & Ikeda K. (2011) Identification of selective agonists and antagonists to g protein-activated inwardly rectifying potassium channels: candidate medicines for drug dependence and pain. Curr Neuropharmacol. 9(1):113-7.
24. Niswender C M et al. (2008) A novel assay of Gi/o-linked G protein-coupled receptor coupling to potassium channels provides new insights into the pharmacology of the group III metabotropic glutamate receptors. Mol Pharmacol. 73(4):1213-24.
25. Kennedy, J P et al. Application of combinatorial chemistry science on modern drug discovery. *J. Comb. Chem.* 2008, 10, 345-354.
26. Rubinstein M et al. (2009) Divergent regulation of GIRK1 and GIRK2 subunits of the neuronal G protein gated K+ channel by Gαi GDP and Gβγ. *J Physiol* 587(14): 3473-3491.
27. Signorini, S., Liao, Y. J., Duncan, S. A., Jan, L. Y. & Stoffel, M. (1997) Normal cerebellar development but susceptibility to seizures in mice lacking G protein-coupled, inwardly rectifying K+ channel GIRK2. *Proc. Natl Acad. Sci. USA* 94, 923-927.
28. Khroyan T V et al. Rodent Motor and Neuropsychological Behavior Measured in Home Cages Using the Integrated Modular Platform—SmartCage™. Clinical and Experimental Pharmacology and Physiology, 2012, 39, 614-622.
29. Kobayashi, T.; Ikeda, K.; Ichikawa, T.; Abe, S.; Togashi, S.; Kumanishi, T. Biochem. Biophys. Res. Commun. 1995, 208, 1166.
30. Karschin, C.; Dissmann, E.; Stuhmer, W.; Karschin, A. J. Neurosci. 1996, 16, 3559.
31. Kaufmann, K., et al., (2013) ML297 (VU0456810), the First Potent and Selective Activator of the GIRK Potassium Channel, Displays Antiepileptic Properties in Mice. *ACS Chemical Neuroscience.* 4, 1278-1286.
32. Lindsley, C. W.; Wisnoski, D. D.; Leister, W. H.; O'Brien, J. A.; Lemiare, W.; Williams, D. L., Jr.; Bumo, M.; Sur, C.; Kinney, G. G.; Pettibone, D. J.; Tiller, P. R.; Smith, S.; Duggan, M. E.; Hartman, G. D.; Conn, P. J.; Huff, J. R. J. Med. Chem. 2004, 47, 5825.
33. Sharma, S.; Rodriguez, A.; Conn, P. J.; Lindsley, C. W. Bioorg. Med. Chem. Lett. 2008, 18, 4098.
34. Wood, M. R.; Hopkins, C. R.; Brogan, J. T.; Conn, P. J.; Lindsley, C. W. Biochemistry 2011, 50, 2403.
35. Cheung, Y.- Y.; Yu, H.; Xu, K.; Zou, B.; Wu, M.; McManus, O. B.; Li, M.; Lindsley, C. W.; Hopkins, C. R. J. Med. Chem. 2012, 55, 6975.
36. Terry, P.; Katz, J. L. Psychopharmacology 1994, 113, 328.
37. O'Neil, S. K.; Bolger, G. T. Brain Res. Bull. 1988, 21, 865.

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:
1. A compound of the formula

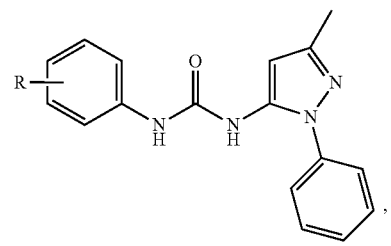

or a pharmaceutically-acceptable salt thereof, wherein R is selected from H, 2-Cl, 3-Cl, 4-Cl, 2-Br, 3-Br, 4-Br, 3-F, 4-F, 2-CF$_3$, 3-CF$_3$, 4-CF$_3$, 3-CH$_3$, 2-SCH$_3$, 3-SO$_2$NH$_2$, 4-SO$_2$NH$_2$, 3-SCH$_3$, 4-SCH$_3$, 2-OCH$_3$, 3-OCH$_3$, 4-OCH$_3$, 3,4-diCl, 3,5-diCl, 2-Cl/6-OCH$_3$, and 3,4-diF.

2. The compound of claim 1, according to the formula

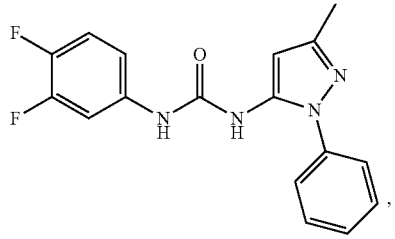 [SMILES: Cc1cc(NC(=O)Nc2ccc(F)c(F)c2)n(-c2ccccc2)n1]

or a pharmaceutically-acceptable salt thereof.

3. The compound of claim 1, wherein the compound activates GIRK channels including a GIRK1 subunit.

4. The compound of claim 1, wherein the compound does not activate GIRK channels that do not include a GIRK1 subunit.

5. The compound of claim 1, wherein the compound activates GIRK channels selected from GIRK1/2, GIRK1/3, and GIRK1/4.

6. A pharmaceutical composition, comprising a pharmaceutically-acceptable carrier; and a compound of claim 1.

7. The pharmaceutical composition claim 6, and further comprising a second compound or composition having GIRK activation activity, or wherein the second compound or composition is useful for treating a condition of interest, selected from addiction and withdrawal behaviors, pain perception, anxiety, spatial learning/memory, and predisposition toward seizure activity.

8. The pharmaceutical composition claim 7, wherein the condition of interest is epilepsy.

9. A method of activating a GIRK potassium channel, comprising contacting a cell with an effective amount of a compound of claim 1.

10. The method of claim 9, wherein contacting the cell with the compound or composition comprises administering the compound or composition to a subject.

11. The method of claim 10, wherein the administration is to a subject in need of treatment for a condition of interest.

12. The method of claim 11, wherein the condition of interest is selected from addiction and withdrawal behaviors, pain perception, anxiety, spatial learning/memory, and predisposition a toward seizure activity.

13. A method of treating epilepsy in a subject in need thereof, comprising administering to the subject an effective amount of a compound of claim 1.

14. The method of claim 13, wherein the compound activates GIRK channels including a GIRK1 subunit.

15. The method of claim 14, wherein the compound activates GIRK channels selected from GIRK1/2, GIRK1/3, and GIRK1/4.

16. A compound of the formula

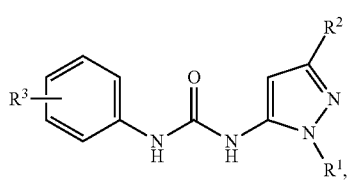

or a pharmaceutically-acceptable salt thereof,
wherein R1 is selected from

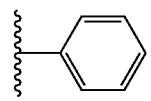

and

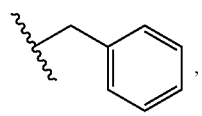 [SMILES: *Cc1ccccc1],

R2 is selected from,

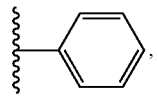, 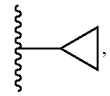, ,

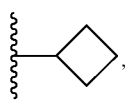, 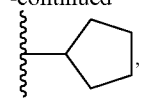, 

and

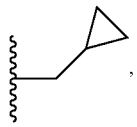, and
R3 is selected from 3-Cl, 3-Br, 3-CH$_3$, 4-CH$_3$, 3-F, 4-F, 3,4-diF, 3-SCH$_3$, 3-CF$_3$, and 3-Cl/4-F.

17. The compound of claim 16, having the formula

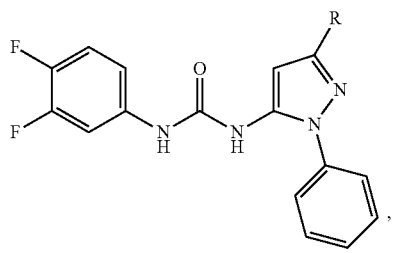

or a pharmaceutically-acceptable salt thereof, wherein R is selected from

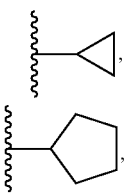, 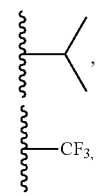,

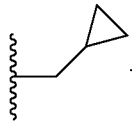 [SMILES: *CC1CC1], 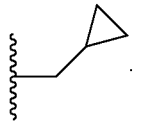, 

and

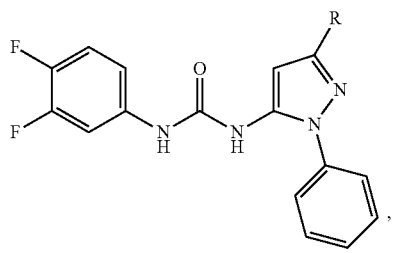.

18. A method of activating a GIRK potassium channel, comprising contacting a cell with an effective amount of a compound of claim 16.

* * * * *